US007244585B1

(12) United States Patent
Sangar et al.

(10) Patent No.: US 7,244,585 B1
(45) Date of Patent: Jul. 17, 2007

(54) 3' SEQUENCE OF THE GB VIRUS B (GBV-B) GENOME

(75) Inventors: David V. Sangar, Burbage Leics (GB); Stanley M. Lemon, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1230 days.

(21) Appl. No.: 09/587,653

(22) Filed: Jun. 5, 2000

Related U.S. Application Data

(60) Provisional application No. 60/137,665, filed on Jun. 4, 1999.

(51) Int. Cl.
| | |
|---|---|
| C12P 19/36 | (2006.01) |
| C12N 15/09 | (2006.01) |
| C12N 15/51 | (2006.01) |
| C12N 7/01 | (2006.01) |
| C07H 19/00 | (2006.01) |

(52) U.S. Cl. .................. 435/69.1; 435/320.1; 435/91.4; 424/228.1; 536/24.1

(58) Field of Classification Search ............ 435/235.1, 435/237, 239, 325, 5, 69.1; 536/23.72, 23.7; 424/204.1, 225.1

See application file for complete search history.

(56) References Cited

U.S. PATENT DOCUMENTS

| 5,672,350 A * | 9/1997 | Parker et al. ............ 424/221.1 |
| 5,807,670 A | 9/1998 | Muerhoff et al. ............... 435/5 |
| 6,627,437 B1 * | 9/2003 | Traboni .................... 435/320.1 |

OTHER PUBLICATIONS

Buckwold et al. Antiviral Research 2005, vol. 66, pp. 165-168.*
Bukh et al. Virol. Sep. 1999, vol. 262, No. 2, pp. 470-478.*
Sbardellati et al. J Gene. Virol. 2001, vol. 82, pp. 2437-2448.*
NCBI AJ277947 p. 1-5.*
The HIV Life Cycle, published by OpenChemist.Net on Jun. 5, 2006, pp. 1-15.*
Brass et al. Int. J. Med. 2006, vol. 3, pp. 29-34.*
Bartenschlager et al. J. Gene. Viro. 2000, vol. 81, pp. 1631-1648.*
Virus Repication published by Microbiology @ Leicester: Virology on Oct. 22, 2004, pp. 1-20.*
The Free Dictionary by FARLEX on line, Google searches on Aug. 11, 2006, pp. 1-2.*
Al et al., "Expression of recombinant hepatitis C virus in non-structural protein 5B *Escherichia coli.*," *Virus Res* 53:141-149, 1998.
Beard et al. "An infectious molecular clone of a japanese genotype 1b hepatitis c virus," *Hepatology*, 30:316-324 1999.
Behrens et al., "Identification and properties of the RNA dependent RNA polymerase of hepatitis C virus," *EMBO J*, 15:12-22, 1996.

Chambers et al., "Yellow fever/Japanese encephalitis chimeric viruses. construction and biological properties," *J Virol*, 73:3095-3101, 1999.
Choo et al., "Vaccination of chimpanzees against infection by the hepatitis C virus," *Proc Natl Acad Sci USA*, 91:1294-1298, 1994.
Farci et al., "Lack of protective immunity against reinfection with hepatitis c virus," *Science*, 258:135-140. 1992.
Farci et al., "The natural history of infection with hepatitis C virus (HCV) in chimpanzees: Comparison of serologic responses measured with first- and second-generation assays and relationship to HCV viremia," *The Journal of Infectious Diseases*, 165:1006-1011, 1992.
Frolov et al., "Cis-acting RNA elements required for replication of bovine viral diarrhea virus-hepatitis C virus 5' nontranslated region chimeras," *RNA* 4:1418-1435, 1998.
Hijikata et al., "Two distinct protease activites required for the processing of a putative nonstructural precursor protein of hepatitis C virus," *J Virol*, 67:4665-4675, 1993.
Honda et al., "Stability of a stem-loop involving the initiator AUG controls the efficiency of internal initiation of translation on hepatits C virus RNA," *RNA*, 2:955-968, 1996.
Karayiannis et al., "Studies of GB hepatitis agent in tamarins," *Hepatology*, 9:186-192, 1989.
Kim et al., "Crystal structure of the hepatitis C virus NS3 protease domain complexed with a synthetic NS4A confactor peptide," *Cell*, 87:343-355, 1996.
Kolykhalov et al., "Transmission of hepatitis C by intrahepatic inoculation of transcribed RNA," *Science*, 277:570-574, 1997.
Kolykhalov et al., "Identification of a highly conserved element at the 3' terminus of hepatitis C virus genome RNA," *J Virol*, 70:3363-3371, 1996.
Lemon and Honda, "Internal ribosome entry sites within the RNA genomes of hepatitis C virus and other flaviviruses," *Seminars in Virology*, 8:274-288, 1997.
Lu and Wimmer, "Poliovirus chimeras replicating under the translational control of genetic elements of hepatitis C virus reveal unusual properties of the internal ribosomal entry site of hepatitis C virus," *Proc Natl Acad Sci USA*, 93:1412-1417, 1996.
Muerhoff et al., "Genomic organisation of GB viruses A and B: Two new members of the flaviviridae associated with GB agent hepatitis," *J Virol*, 69:5621-5630, 1995.
Pletnev et al., "Construction and characterization of chimeric tick-borne encephalitis/dengue type 4 viruses," *Proc. Natl Acad Sci USA*, 89:10532-10536, 1992.

(Continued)

*Primary Examiner*—Bruce R. Campell
*Assistant Examiner*—Qun Li Bao
(74) *Attorney, Agent, or Firm*—Fulbright & Jaworski L.L.P.

(57) ABSTRACT

The present invention relates generally to the fields of biochemistry, molecular biology, and virology. More particularly, it relates to the identification of 259 nucleotides located at the 3' end of the GB virus B (GBV-B) genome. The invention involves nucleic acid constructs and compositions encoding GBV-B sequence, including the 3' end of the sequence, which has allowed an infectious GBV-B clone to be constructed. This construct, and chimeric versions of it, may be employed to study GBV-B and related hepatitis family members, such as hepatitis C virus. The invention thus includes methods of preparing GBV-B-containing sequences, constructs, and viruses, as well as methods of employing these compositions.

25 Claims, 1 Drawing Sheet

OTHER PUBLICATIONS

Reynolds et al., "Unique features of internal initiation of hepatitis C virus RNA translation," *EMBO J*, 14:6010-6020, 1995.

Rijnbrand et al., "Mutational analysis of the GB virus B internal ribosome entry site," *J Virol*, 74:773-783, 2000.

Scarselli et al., "GB virus B and hepatitis C virus share substrate specificity," *J Virol*, 74:4985-4989, 1997.

Schlauder et al., "Molecular and serological analysis in the transmission of the GB hepatitis agent," *J Med Virol*, 46:81-90, 1995.

Shaffer et al., "A hepatitis A virus deletion mutant which lacks the first pyrimidine-rich tract of the 5' nontranslated RNA remains virulent in primates after direct intrahepatic nucleic acid transfection," *J Virol*, 69:6600-6604, 1995.

Simons et al., "Identification of two flavivirus like genomes in the GB hepatitis agent," *Proc Natl Acad Sci*, 92:3401-3405, 1995.

Tanaka et al., "A novel sequence found at the 3' terminus of hepatitis C virus genome," *Biochem Biophys Res Comm*, 215:744-749, 1995.

Todd et al., "Replication competent picornaviruses with complete genomic RNA 3' non-coding deletions," *J Virol*, 71:8868-8874, 1997.

Yanagi et al., "Transcripts from a single full length cdna clone of hepatitius c virus are infectious when directly transfected into a liver of a chimpanzee," *Proc Natl Acad Sci USA*, 94:8738-8743, 1998.

Yao et al., "Structure of the hepatitis C virus RNA helicase domain," *Nature Structural Biology*, 4:463-467, 1997.

Zhao et al., "Poliovirus/hepatitis C virus (internal ribosome entry site-core) chimeric viruses: improved growth properties through modification of a proteolytic cleavage site and requirement for core RNA sequence but not for core related polypeptides," *J Virol*, 73:1546-1554, 1999.

* cited by examiner

SEQUENCE LISTING

```
<160> NUMBER OF SEQ ID NOS: 17

<210> SEQ ID NO 1
<211> LENGTH: 260
<212> TYPE: RNA
<213> ORGANISM: Unknown
<220> FEATURE:
<223> OTHER INFORMATION: Description of Unknown Organism:  GB VIRUS B

<400> SEQUENCE: 1
gaguuugcga ccauggugga ucagaaccgu uucggugaa gccauggucu gaaggggaug       60
acgucccuuc uggcucaucc acaaaaaccg ucucgggugg gugaggaguc cuggcugugu      120
gggaagcagu caguauaauu cccgucgugu guggugacgc cucacgacgu auuuguccgc      180
ugugcagagc guaguaccaa gggcugcacc ccgguuuuug uuccaagcgg agggcaaccc      240
ccgcuuggaa uuaaaaacug                                                 260

<210> SEQ ID NO 2
<211> LENGTH: 9399
<212> TYPE: DNA
<213> ORGANISM: GBV-A-like virus

<400> SEQUENCE: 2
accacaaaca ctccagtttg ttacactccg ctaggaatgc tcctggagca ccccccctag       60
cagggcgtgg gggatttccc ctgcccgtct gcagaagggt ggagccaacc accttagtat      120
gtaggcggcg ggactcatga cgctcgcgtg atgacaagcg ccaagcttga cttggatggc      180
cctgatgggc gttcatgggt tcggtggtgg tggcgcttta ggcagcctcc acgcccacca      240
cctcccagat agagcggcgg cactgtaggg aagaccgggg accggtcact accaaggacg      300
cagacctctt tttgagtatc acgcctccgg aagtagttgg gcaagcccac ctatatgtgt      360
tgggatggtt ggggttagcc atccataccg tactgcctga tagggtcctt gcgaggggat      420
ctgggagtct cgtagaccgt agcacatgcc tgttatttct actcaaacaa gtcctgtacc      480
tgcgcccaga acgcgcaaga acaagcagac gcaggcttca tatcctgtgt ccattaaaac      540
atctgttgaa aggggacaac gagcaaagcg caaagtccag cgcgatgctc ggcctcgtaa      600
ttacaaaatt gctggtatcc atgatggctt gcagacattg gctcaggctg ctttgccagc      660
tcatggttgg ggacgccaag accctcgcca taagtctcgc aatcttggaa tccttctgga      720 ttacccttg gggtggattg gtgatgttac aactcacaca cctctagtag gcccgctggt      780
ggcaggagcg gtcgttcgac cagtctgcca gatagtacgc ttgctggagg atggagtcaa      840
```

```
ctgggctact ggttggttcg gtgtccacct ttttgtggta tgtctgctat ctttggcctg    900
tccctgtagt ggggcgcggg tcactgaccc agacacaaat accacaatcc tgaccaattg    960
ctgccagcgt aatcaggtta tctattgttc tccttccact tgcctacacg agcctggttg   1020
tgtgatctgt gcggacgagt gctgggttcc cgccaatccg tacatctcac acccttccaa   1080
ttggactggc acggactcct tcttggctga ccacattgat tttgttatgg gcgctcttgt   1140
gacctgtgac gcccttgaca ttggtgagtt gtgtggtgcg tgtgtattag tcggtgactg   1200
gcttgtcagg cactggctta ttcacataga cctcaatgaa actggtactt gttacctgga   1260
agtgcccact ggaatagatc ctgggttcct agggtttatc gggtggatgg ccggcaaggt   1320
cgaggctgtc atcttcttga ccaaactggc ttcacaagta ccatacgcta ttgcgactat   1380
gtttagcagt gtacactacc tggcggttgg cgctctgatc tactatgcct ctcggggcaa   1440
gtggtatcag ttgctcctag cgcttatgct ttacatagaa gcgacctctg aaaccctat    1500
cagggtgccc actggatgct caatagctga gttttgctcg cctttgatga taccatgtcc   1560
ttgccactct tatttgagtg agaatgtgtc agaagtcatt tgttacagtc aaagtggac    1620
caggcctatc actctagagt ataacaactc catatcttgg taccccctata caatccctgg   1680
tgcgagggga tgtatggtta aattcaaaaa taacacatgg ggttgctgcc gtattcgcaa   1740
tgtgccatcg tactgcacta tgggcactga tgcagtgtgg aacgacactc gcaacactta   1800
cgaagtatgc ggtgtaacac catggctaac aaccgcatgg cacaacggct cagccctgaa   1860
attggctata ttacaatacc ctgggtctaa agaaatgttt aaacctcata attggatgtc   1920
aggccatttg tattttgagg gatcagatac ccctatagtt tacttttatg accctgtgaa   1980
ttccactctc ctaccaccgg agaggtgggc taggttgccc ggtaccccac ctgtggtacg   2040
tggttcttgg ttacaggttc cgcaagggtt ttacagtgat gtgaaagacc tagccacagg   2100
attgatcacc aaagacaaag cctggaaaaa ttatcaggtc ttatattccg ccacgggtgc   2160
tttgtctctt acgggagtta ccaccaaggc cgtggtgcta attctgttgg ggttgtgtgg   2220
cagcaagtat cttatttag cctacctctg ttacttgtcc ctttgttttg ggcgcgcttc    2280
tggttaccct ttgcgtcctg tgctcccatc ccagtcgtat ctccaagctg ctgggatgt    2340
tttgtctaaa gctcaagtag ctcccttttgc tttgattttc ttcatctgtt gctatctccg   2400
ctgcaggcta cgttatgctg ccccttttagg gtttgtgccc atggctgcgg gcttgcccct   2460
aactttcttt gttgcagcag ctgctgccca accagattat gactggtggg tgcgactgct   2520
agtggcaggg ttagttttgt gggccggccg taaccgtggt caccgcatag ctctgcttgt   2580
aggtccttgg cctctggtag cgcttttaac cctcttgcat ttggttacgc ctgcttcagc   2640
ttttgatacc gagataattg gagggctgac aataccacct gtagtagcat tagttgtcat   2700
gtctcgtttt ggcttctttg ctcacttgtt acctcgctgt gctttagtta actcctatct   2760
ttggcaacgt tgggagaatt ggttttggaa cgttacacta agaccggaga ggttttttcct  2820
tgtgctggtt tgtttcccccg gtgcgacata tgacgcgctg gtgactttct gtgtgtgtca   2880
cgtagctctt ctatgtttaa catccagtgc agcatcgttc tttgggactg actctagggt   2940
tagggcccat agaatgttgg tgcgtctcgg aaagtgtcat gcttggtatt ctcattatgt   3000
tcttaagttt ttcctcttag tgtttggtga gaatggtgtg ttttttctata agcacttgca   3060
tggtgatgtc ttgcctaatg attttgcctc gaaactacca ttgcaagagc cattttttccc  3120
ttttgaaggc aaggcaaggg tctataggaa tgaaggaaga cgcttggcgt gtggggacac   3180
```

-continued

```
ggttgatggt tgcccgttg ttgcgcgtct cggcgacctt gttttcgcag ggttggctat    3240
gccgccagat gggtgggcca ttaccgcacc ttttacgctg cagtgtctct ctgaacgtgg    3300
cacgctgtca gcgatggcag tggtcatgac tggtatagac ccccgaactt ggactggaac    3360
tatcttcaga ttaggatctc tggccactag ctacatggga tttgtttgtg acaacgtgtt    3420
gtatactgct caccatggca gcaaggggcg ccggttggct catcccacag gctctataca    3480
cccaataacc gttgacgcgg ctaatgacca ggacatctat caaccaccat gtggagctgg    3540
gtcccttact cggtgctctt gcggggagac caagggtat ctggtaacac gactggggtc    3600
attggttgag gtcaacaaat ccgatgaccc ttattggtgt gtgtgcgggg cccttcccat    3660
ggctgttgcc aagggttctt caggtgcccc gattctgtgc tcctccgggc atgttattgg    3720
gatgttcacc gctgctagaa attctggcgg ttcagtcagt cagattaggg ttaggccgtt    3780
ggtgtgtgct ggataccatc cccagtacac agcacatgcc actcttgata caaaacctac    3840
tgtgcctaac gagtattcag tgcaaatttt aattgccccc actggcagcg gcaagtcaac    3900
caaattacca ctttcttaca tgcaggagaa gtatgaggtc ttggtcctaa atcccagtgt    3960
ggctacaaca gcatcaatgc caaagtacat gcacgcgacg tacggcgtga atccaaattg    4020
ctattttaat ggcaaatgta ccaacacagg ggcttcactt acgtacagca catatggcat    4080
gtacctgacc ggagcatgtt cccggaacta tgatgtaatc atttgtgacg aatgccatgc    4140
taccgatgca accaccgtgt gggcattgg aaaggtccta accgaagctc catccaaaaa    4200
tgttaggcta gtggttcttg ccacggctac ccccctgga gtaatcccta caccacatgc    4260
caacataact gagattcaat taaccgatga aggcactatc ccctttcatg gaaaaaagat    4320
taaggaggaa aatctgaaga aagggagaca cctatctttt gaggctacca aaaacactg    4380 tgatgagctt gctaacgagt tagctcgaaa gggaataaca gctgtctctt actatagggg    4440
atgtgacatc tcaaaaatcc ctgagggcga ctgtgtagta gttgccactg atgccttgtg    4500
tacagggtac actggtgact ttgattccgt gtatgactgc agcctcatgg tagaaggcac    4560
atgccatgtt gaccttgacc ctactttcac catgggtgtt cgtgtgtgcg ggtttcagc    4620 aatagttaaa ggccagcgta ggggccgcac aggccgtggg agagctggca tatactacta    4680
tgtagacggg agttgtaccc cttcgggtat ggttcctgaa tgcaacattg ttgaagcctt    4740
cgacgcagcc aaggcatggt atggtttgtc atcaacagaa gctcaaacta ttctggacac    4800
ctatcgcacc caacctgggt tacctgcgat aggagcaaat ttggacgagt gggctgatct    4860
cttttctatg gtcaaccccg aaccttcatt tgtcaatact gcaaaaagaa ctgctgacaa    4920
ttatgttttg ttgactgcag cccaactaca actgtgtcat cagtatgct atgctgctcc    4980 caatgacgca ccacggtggc agggagcccg gcttgggaaa aaaccttgtg gggttctgtg    5040
gcgcttggac ggcgctgacg cctgtcctgg cccagagccc agcgaggtga ccagatacca    5100
aatgtgcttc actgaagtca atacttctgg gacagccgca ctcgctgttg gcgttggagt    5160
ggctatggct tatctagcca ttgacacttt tggcgccact tgtgtgcggc gttgctggtc    5220
tattgcatca gtccctaccg gtgctactgt cgccccagtg gttgacgaag aagaaatcgt    5280
ggaggagtgt gcatcattca ttcccttgga ggccatggtt gctgcaatcg ataagctgaa    5340
gagtacaatc accacaacta gtccttcac attggaaacc gcccttgaaa acttaacac    5400 ctttcttggg cctcatgcag ctacaatcct tgctatcata gagtattgct gtggtttagt    5460
cactttacct gacaatccct ttgcatcatg cgtgtttgct ttcattgcgg gtattactac    5520
cccactacct cacaagatca aaatgttcct gtcattattt ggaggcgcaa ttgcgtccaa    5580
```

```
gcttacagac gctagaggcg cactggcgtt catgatggcc ggggctgcgg gaacagctct   5640
tggtacatgg acatcggtgg gttttgtctt tgacatgcta ggcggctatg ctgccgcctc   5700
atccactgct tgcttgacat ttaaatgctt gatgggtgag tggcccacta tggatcagct   5760
tgctggttta gtctactccg cgttcaatcc ggccgcagga gttgtgggcg tcttgtcagc   5820
ttgtgcaatg tttgctttga caacagcagg gccagatcac tggcccaaca gacttcttac   5880
tatgcttgct aggagcaaca ctgtatgtaa tgagtacttt attgccactc gtgacatccg   5940
caggaagata ctgggcattc tggaggcatc taccccctgg agtgtcatat cagcttgcat   6000
ccgttggctc cacaccccga cggaggatga ttgcggcctc attgcttggg gtctagagat   6060
ttggcagtat gtgtgcaatt tctttgtgat ttgctttaat gtccttaaag ctggagttca   6120
gagcatggtt aacattcctg ttgtcctttc tacagctgc cagaagggt acaagggccc     6180
ctggattgga tcaggtatgc tccaagcacg ctgtccatgc ggtgctgaac tcatcttttc   6240
tgttgagaat ggttttgcaa aactttacaa aggacccaga acttgttcaa attactggag   6300
aggggctgtt ccagtcaacg ctaggctgtg tgggtcggct agaccggacc caactgattg   6360
gactagtctt gtcgtcaatt atggcgttag ggactactgt aaatatgaga aatgggaga    6420
tcacattttt gttacagcag tatcctctcc aaatgtctgt ttcacccagg tgccccaac    6480
cttgagagct gcagtggccg tggacggcgt acaggttcag tgttatctag gtgagcccaa   6540
aactccttgg acgacatctg cttgctgtta cggtcctgac ggtaagggta aaactgttaa   6600
gcttcccttc cgcgttgacg gtcacacacc tggtgtgcgc atgcaactta atttgcgtga   6660
tgcacttgag acaaatgact gtaattccac aaacaacact cctagtgatg aagccgcagt   6720
gtccgctctt gttttcaaac aggagttgcg gcgtacaaac caattgcttg aggcaatttc   6780
agctggcgtt gacaccacca aactgccagc cccctccatc gaagaggtag tggtaagaaa   6840
gcgccagttc cgggcaagaa ctggttcgct taccttgcct ccccctccga gatccgtccc   6900
aggagtgtca tgtcctgaaa gcctgcaacg aagtgacccg ttagaaggtc cttcaaacct   6960
ccctccttca ccacctgttc tacagttggc catgccgatg cccctgttgg gagcgggtga   7020
gtgtaaccct ttcactgcaa ttggatgtgc aatgaccgaa acaggcggag gccctgatga   7080
tttacccagt taccctccca aaaggaggt ctctgaatgg tcagacgaaa gttggtcgac    7140
ggctacaacc gtttccagct acgttactgg ccccccgtac cctaagatac ggggaaagga   7200
ttccactcag tcagccccg ccaaacggcc tacaaaaaag aagttgggaa agagtgagtt    7260
ttcgtgcagc atgagctaca cctggaccga cgtgattagc ttcaaaactg cttctaaagt   7320
tctgtctgca actcgggcca tcactagtgg ttttcctcaaa caaagatcat tggtgtatgt   7380
gactgagccg cgggatgcgg agcttagaaa acaaaaagtc actattaata gacaacctct   7440
gttcccccca tcataccaca agcaagtgag attggctaag gaaaaagctt caaaagttgt   7500
cggtgtcatg tgggactatg atgaagtagc agctcacacg ccctctaagt ctgctaagtc   7560
ccacatcact ggccttcggg gcactgatgt tcgttctgga gcagcccgca aggctgttct   7620
ggacttgcag aagtgtgtcg aggcaggtga gataccgagt cattatcggc aaactgtgat   7680
agttccaaag gaggaggtct tcgtgaagac cccccagaaa ccaacaaaga acccccaag    7740
gcttatctcg taccccccacc ttgaaatgag atgtgttgag aagatgtact acggtcaggt   7800
tgctcctgac gtagttaaag ctgtcatggg agatgcgtac gggtttgtag atccacgtac   7860
ccgtgtcaag cgtctgttgt cgatgtggtc acccgatgca gtcggagcca catgcgatac   7920
```

```
agtgtgtttt gacagtacca tcacacccga ggatatcatg gtggagacag acatctactc    7980
agcagctaaa ctcagtgacc aacaccgagc tggcattcac accattgcga ggcagttata    8040
cgctggagga ccgatgatcg cttatgatgg ccgagagatc ggatatcgta ggtgtaggtc    8100
ttccggcgtc tatactacct caagttccaa cagtttgacc tgctggctga aggtaaatgc    8160
tgcagccgaa caggctggca tgaagaaccc tcgcttcctt atttgcggcg atgattgcac    8220
cgtaatttgg aagagcgccg gagcagatgc agacaaacaa gcaatgcgtg tctttgctag    8280
ctggatgaag gtgatgggtg caccacaaga ttgtgtgcct caacccaaat acagtttgga    8340
agaattaaca tcatgctcat caaatgttac ctctggaatt accaaaagtg caagcctta    8400 ctactttctt acaagagatc ctcgtatccc ccttggcagg tgctctgccg agggtctggg    8460
atacaacccc agtgctgcgt ggattgggta tctaatacat cactacccat gtttgtgggt    8520
tagccgtgtg ttggctgtcc atttcatgga gcagatgctc tttgaggaca aacttcccga    8580
gacggtgacc tttgactggt atgggaaaaa ttatacggtg cctgtagaag atctgcccag    8640
catcattgct ggtgtgcacg gtattgaggc tttctcggtg gtgcgctaca ccaacgctga    8700
gatcctcaga gtttcccaat cactaacaga catgaccatg ccccccctgc gagcctggcg    8760
aaagaaagcc agggcggtcc tcgccagcgc caagaggcgt ggcggagcac acgcaaaatt    8820
ggctcgcttc cttctctggc atgctacatc tagacctcta ccagatttgg ataagacgag    8880
cgtggctcgg tacaccactt tcaattattg tgatgtttac tccccggagg gggatgtgtt    8940
tattacacca cagagaagat tgcagaagtt tcttgtgaag tatttggctg tcattgtttt    9000
tgccctaggg ctcattgctg ttggattagc catcagctga accccaaat tcaaaattaa    9060 ctaacagttt tttttttttt tttttttttt agggcagcgg caacagggga gaccccgggc    9120
ttaacgaccc cgccgatgtg agtttggcga ccatggtgga tcagaaccgt tcgggtgaa    9180 gccatggtct gaaggggatg acgtcccttc tggctcatcc acaaaaaccg tctcgggtgg    9240
gtgaggagtc ctggctgtgt gggaagcagt cagtataatt cccgtcgtgt gtggtgacgc    9300
ctcacgacgt atttgtccgc tgtgcagagc gtagtaccaa gggctgcacc ccggtttttg    9360
ttccaagcgg agggcaaccc ccgcttggaa ttaaaaact                           9399

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence:   Primer

<400> SEQUENCE: 3
cgggatcccg taatacgact cactatagac cacaaacact ccagtttg               48

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:   Primer

<400> SEQUENCE: 4
gtggaattca cagcgtcata                                              20

<210> SEQ ID NO 5
<211> LENGTH: 21
<212> TYPE: DNA
<213> ORGANISM: Artificial Sequence
```

```
<220> FEATURE:
<223> OTHER INFORMATION: Description of Artificial Sequence: Primer

<400> SEQUENCE: 5
tgtgaattcc actctcctac c                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
ttatcgattg cagcaaccat g                                              21

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 7
catggttgct gcaatcgata agctgaagag tacaataac                           39

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
gacaacagac gcttgacacg                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
ctgtcatggg agatgcgtac                                                20

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 10
cgagctcgag cacatcgcgg ggtcgttaag cccggggtct cc                       42

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
gacaacagac gcttgacacg                                                20
```

```
<210> SEQ ID NO 12
<211> LENGTH: 108
<212> TYPE: DNA
<213> ORGANISM: Artificial Sequence
<220> FEATURE:
<223> OTHER INFORMATION: Description of Artificial Sequence: Primer

<400> SEQUENCE: 12
ccgactcgag aattcggccc tgcaggccac aacagtctcg cgagttttta attccaagcg      60
ggggttgccc tccgcttgga acaaaaaccg gggtgcagcc cttggtac                 108

<210> SEQ ID NO 13
<211> LENGTH: 9599
<212> TYPE: DNA
<213> ORGANISM: Hepatitis C virus
<220> FEATURE:
<221> NAME/KEY: CDS
<222> LOCATION: (342)..(9377)

<400> SEQUENCE: 13
gccagccccc tgatggggggc gacactccac catgaatcac tcccctgtga ggaactactg     60
tcttcacgca gaaagcgtct agccatggcg ttagtatgag tgtcgtgcag cctccaggac    120 ccccccctccc gggagagcca tagtggtctg cggaaccggt gagtacaccg gaattgccag    180
gacgaccggg tcctttcttg gataaaaccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac c atg agc acg aat cct    356
                                             Met Ser Thr Asn Pro
                                               1               5 aaa cct caa aga aaa acc aaa cgt aac acc aac cgt cgc cca cag gac      404
Lys Pro Gln Arg Lys Thr Lys Arg Asn Thr Asn Arg Arg Pro Gln Asp
                 10                  15                  20 gtc aag ttc ccg ggt ggc ggt cag atc gtt ggt gga gtt tac ttg ttg      452
Val Lys Phe Pro Gly Gly Gly Gln Ile Val Gly Gly Val Tyr Leu Leu
             25                  30                  35 ccg cgc agg ggc cct aga ttg ggt gtg cgc gcg acg agg aag act tcc      500
Pro Arg Arg Gly Pro Arg Leu Gly Val Arg Ala Thr Arg Lys Thr Ser
         40                  45                  50 gag cgg tcg caa cct cga ggt aga cgt cag cct atc ccc aag gca cgt      548
Glu Arg Ser Gln Pro Arg Gly Arg Arg Gln Pro Ile Pro Lys Ala Arg
     55                  60                  65 cgg ccc gag ggc agg acc tgg gct cag ccc ggg tac cct tgg ccc ctc      596
Arg Pro Glu Gly Arg Thr Trp Ala Gln Pro Gly Tyr Pro Trp Pro Leu
 70                  75                  80                  85 tat ggc aat gag ggt tgc ggg tgg gcg gga tgg ctc ctg tct ccc cgt      644
Tyr Gly Asn Glu Gly Cys Gly Trp Ala Gly Trp Leu Leu Ser Pro Arg
                 90                  95                 100 ggc tct cgg cct agc tgg ggc ccc aca gac ccc cgg cgt agg tcg cgc      692
Gly Ser Arg Pro Ser Trp Gly Pro Thr Asp Pro Arg Arg Arg Ser Arg
            105                 110                 115 aat ttg ggt aag gtc atc gat acc ctt acg tgc ggc ttc gcc gac ctc      740
Asn Leu Gly Lys Val Ile Asp Thr Leu Thr Cys Gly Phe Ala Asp Leu
        120                 125                 130 atg ggg tac ata ccg ctc gtc ggc gcc cct ctt gga ggc gct gcc agg      788
Met Gly Tyr Ile Pro Leu Val Gly Ala Pro Leu Gly Gly Ala Ala Arg
    135                 140                 145 gcc ctg gcg cat ggc gtc cgg gtt ctg gaa gac ggc gtg aac tat gca      836
Ala Leu Ala His Gly Val Arg Val Leu Glu Asp Gly Val Asn Tyr Ala
150                 155                 160                 165
```

```
aca ggg aac ctt cct ggt tgc tct ttc tct atc ttc ctt ctg gcc ctg      884
Thr Gly Asn Leu Pro Gly Cys Ser Phe Ser Ile Phe Leu Leu Ala Leu
            170                 175                 180 ctc tct tgc ctg act gtg ccc gct tca gcc tac caa gtg cgc aat tcc      932
Leu Ser Cys Leu Thr Val Pro Ala Ser Ala Tyr Gln Val Arg Asn Ser
        185                 190                 195 tcg ggg ctt tac cat gtc acc aat gat tgc cct aac tcg agt att gtg      980
Ser Gly Leu Tyr His Val Thr Asn Asp Cys Pro Asn Ser Ser Ile Val
200                 205                 210 tac gag gcg gcc gat gcc atc ctg cac act ccg ggg tgt gtc cct tgc     1028
Tyr Glu Ala Ala Asp Ala Ile Leu His Thr Pro Gly Cys Val Pro Cys
            215                 220                 225 gtt cgc gag ggt aac gcc tcg agg tgt tgg gtg gcg gtg acc ccc acg     1076
Val Arg Glu Gly Asn Ala Ser Arg Cys Trp Val Ala Val Thr Pro Thr
230                 235                 240                 245 gtg gcc acc agg gac ggc aaa ctc ccc aca acg cag ctt cga cgt cat     1124
Val Ala Thr Arg Asp Gly Lys Leu Pro Thr Thr Gln Leu Arg Arg His
                250                 255                 260 atc gat ctg ctt gtc ggg agc gcc acc ctc tgc tcg gcc ctc tac gtg     1172
Ile Asp Leu Leu Val Gly Ser Ala Thr Leu Cys Ser Ala Leu Tyr Val
            265                 270                 275 ggg gac ctg tgc ggg tct gtc ttt ctt gtt ggt caa ctg ttt acc ttc     1220
Gly Asp Leu Cys Gly Ser Val Phe Leu Val Gly Gln Leu Phe Thr Phe
        280                 285                 290 tct ccc agg cgc cac tgg acg acg caa gac tgc aat tgt tct atc tat     1268
Ser Pro Arg Arg His Trp Thr Thr Gln Asp Cys Asn Cys Ser Ile Tyr
    295                 300                 305 ccc ggc cat ata acg ggt cat cgc atg gca tgg gat atg atg atg aac     1316
Pro Gly His Ile Thr Gly His Arg Met Ala Trp Asp Met Met Met Asn
310                 315                 320                 325 tgg tcc cct acg gca gcg ttg gtg gta gct cag ctg ctc cgg atc cca     1364
Trp Ser Pro Thr Ala Ala Leu Val Val Ala Gln Leu Leu Arg Ile Pro
                330                 335                 340 caa gcc atc atg gac atg atc gct ggt gct cac tgg gga gtc ctg gcg     1412
Gln Ala Ile Met Asp Met Ile Ala Gly Ala His Trp Gly Val Leu Ala
            345                 350                 355 ggc ata gcg tat ttc tcc atg gtg ggg aac tgg gcg aag gtc ctg gta     1460
Gly Ile Ala Tyr Phe Ser Met Val Gly Asn Trp Ala Lys Val Leu Val
        360                 365                 370 gtg ctg ctg cta ttt gcc ggc gtc gac gcg gaa acc cac gtc acc ggg     1508
Val Leu Leu Leu Phe Ala Gly Val Asp Ala Glu Thr His Val Thr Gly
375                 380                 385 gga aat gcc ggc cgc acc acg gct ggg ctt gtt ggt ctc ctt aca cca     1556
Gly Asn Ala Gly Arg Thr Thr Ala Gly Leu Val Gly Leu Leu Thr Pro
390                 395                 400                 405 ggc gcc aag cag aac atc caa ctg atc aac acc aac ggc agt tgg cac     1604
Gly Ala Lys Gln Asn Ile Gln Leu Ile Asn Thr Asn Gly Ser Trp His
                410                 415                 420 atc aat agc acg gcc ttg aat tgc aat gaa agc ctt aac acc ggc tgg     1652
Ile Asn Ser Thr Ala Leu Asn Cys Asn Glu Ser Leu Asn Thr Gly Trp
            425                 430                 435 tta gca ggg ctc ttc tat caa cac aaa ttc aac tct tca ggc tgt cct     1700
Leu Ala Gly Leu Phe Tyr Gln His Lys Phe Asn Ser Ser Gly Cys Pro
        440                 445                 450 gag agg ttg gcc agc tgc cga cgc ctt acc gat ttt gcc cag ggc tgg     1748
Glu Arg Leu Ala Ser Cys Arg Arg Leu Thr Asp Phe Ala Gln Gly Trp
    455                 460                 465 ggt cct atc agt tat gcc aac gga agc ggc ctc gac gaa cgc ccc tac     1796
Gly Pro Ile Ser Tyr Ala Asn Gly Ser Gly Leu Asp Glu Arg Pro Tyr
470                 475                 480                 485
```

-continued

```
tgc tgg cac tac cct cca aga cct tgt ggc att gtg ccc gca aag agc    1844
Cys Trp His Tyr Pro Pro Arg Pro Cys Gly Ile Val Pro Ala Lys Ser
            490                 495                 500 gtg tgt ggc ccg gta tat tgc ttc act ccc agc ccc gtg gtg gtg gga    1892
Val Cys Gly Pro Val Tyr Cys Phe Thr Pro Ser Pro Val Val Val Gly
        505                 510                 515 acg acc gac agg tcg ggc gcg cct acc tac agc tgg ggt gca aat gat    1940
Thr Thr Asp Arg Ser Gly Ala Pro Thr Tyr Ser Trp Gly Ala Asn Asp
    520                 525                 530 acg gat gtc ttc gtc ctt aac aac acc agg cca ccg ctg ggc aat tgg    1988
Thr Asp Val Phe Val Leu Asn Asn Thr Arg Pro Pro Leu Gly Asn Trp
535                 540                 545 ttc ggt tgt acc tgg atg aac tca act gga ttc acc aaa gtg tgc gga    2036
Phe Gly Cys Thr Trp Met Asn Ser Thr Gly Phe Thr Lys Val Cys Gly
550                 555                 560                 565 gcg ccc cct tgt gtc atc gga ggg gtg ggc aac aac acc ttg ctc tgc    2084
Ala Pro Pro Cys Val Ile Gly Gly Val Gly Asn Asn Thr Leu Leu Cys
                570                 575                 580 ccc act gat tgc ttc cgc aaa cat ccg gaa gcc aca tac tct cgg tgc    2132
Pro Thr Asp Cys Phe Arg Lys His Pro Glu Ala Thr Tyr Ser Arg Cys
            585                 590                 595 ggc tcc ggt ccc tgg att aca ccc agg tgc atg gtc gac tac ccg tat    2180
Gly Ser Gly Pro Trp Ile Thr Pro Arg Cys Met Val Asp Tyr Pro Tyr
        600                 605                 610 agg ctt tgg cac tat cct tgt acc atc aat tac acc ata ttc aaa gtc    2228
Arg Leu Trp His Tyr Pro Cys Thr Ile Asn Tyr Thr Ile Phe Lys Val
    615                 620                 625 agg atg tac gtg gga ggg gtc gag cac agg ctg gaa gcg gcc tgc aac    2276
Arg Met Tyr Val Gly Gly Val Glu His Arg Leu Glu Ala Ala Cys Asn
630                 635                 640                 645 tgg acg cgg ggc gaa cgc tgt gat ctg gaa gac agg gac agg tcc gag    2324
Trp Thr Arg Gly Glu Arg Cys Asp Leu Glu Asp Arg Asp Arg Ser Glu
                650                 655                 660 ctc agc ccg ttg ctg ctg tcc acc aca cag tgg cag gtc ctt ccg tgt    2372
Leu Ser Pro Leu Leu Leu Ser Thr Thr Gln Trp Gln Val Leu Pro Cys
            665                 670                 675 tct ttc acg acc ctg cca gcc ttg tcc acc ggc ctc atc cac ctc cac    2420
Ser Phe Thr Thr Leu Pro Ala Leu Ser Thr Gly Leu Ile His Leu His
        680                 685                 690 cag aac att gtg gac gtg cag tac ttg tac ggg gta ggg tca agc atc    2468
Gln Asn Ile Val Asp Val Gln Tyr Leu Tyr Gly Val Gly Ser Ser Ile
    695                 700                 705 gcg tcc tgg gcc att aag tgg gag tac gtc gtt ctc ctg ttc ctt ctg    2516
Ala Ser Trp Ala Ile Lys Trp Glu Tyr Val Val Leu Leu Phe Leu Leu
710                 715                 720                 725 ctt gca gac gcg cgc gtc tgc tcc tgc ttg tgg atg atg tta ctc ata    2564
Leu Ala Asp Ala Arg Val Cys Ser Cys Leu Trp Met Met Leu Leu Ile
                730                 735                 740 tcc caa gcg gag gcg gct ttg gag aac ctc gta ata ctc aat gca gca    2612
Ser Gln Ala Glu Ala Ala Leu Glu Asn Leu Val Ile Leu Asn Ala Ala
            745                 750                 755 tcc ctg gcc ggg acg cac ggt ctt gtg tcc ttc ctc gtg ttc ttc tgc    2660
Ser Leu Ala Gly Thr His Gly Leu Val Ser Phe Leu Val Phe Phe Cys
        760                 765                 770 ttt gcg tgg tat ctg aag ggt agg tgg gtg ccc gga gcg gtc tac gcc    2708
Phe Ala Trp Tyr Leu Lys Gly Arg Trp Val Pro Gly Ala Val Tyr Ala
    775                 780                 785 ctc tac ggg atg tgg cct ctc ctc ctg ctc ctg ctg gcg ttg cct cag    2756
Leu Tyr Gly Met Trp Pro Leu Leu Leu Leu Leu Leu Ala Leu Pro Gln
```

-continued

| | |
|---|---|
| cgg gca tac gca ctg gac acg gag gtg gcc gcg tcg tgt ggc ggc gtt<br>Arg Ala Tyr Ala Leu Asp Thr Glu Val Ala Ala Ser Cys Gly Gly Val<br>                810                           815                        820 | 2804 |
| gtt ctt gtc ggg tta atg gcg ctg act ctg tcg cca tat tac aag cgc<br>Val Leu Val Gly Leu Met Ala Leu Thr Leu Ser Pro Tyr Tyr Lys Arg<br>                      825                          830 | 2852 |
| tat atc agc tgg tgc atg tgg tgg ctt cag tat ttt ctg acc aga gta<br>Tyr Ile Ser Trp Cys Met Trp Trp Leu Gln Tyr Phe Leu Thr Arg Val<br>        840                          845                        850 | 2900 |
| gaa gcg caa ctg cac gtg tgg gtt ccc ccc ctc aac gtc cgg ggg ggg<br>Glu Ala Gln Leu His Val Trp Val Pro Pro Leu Asn Val Arg Gly Gly<br>855                          860                        865 | 2948 |
| cgc gat gcc gtc atc tta ctc atg tgt gta gta cac ccg acc ctg gta<br>Arg Asp Ala Val Ile Leu Leu Met Cys Val Val His Pro Thr Leu Val<br>870                          875                        880                        885 | 2996 |
| ttt gac atc acc aaa cta ctc ctg gcc atc ttc gga ccc ctt tgg att<br>Phe Asp Ile Thr Lys Leu Leu Leu Ala Ile Phe Gly Pro Leu Trp Ile<br>                      890                          895                        900 | 3044 |
| ctt caa gcc agt ttg ctt aaa gtc ccc tac ttc gtg cgc gtt caa ggc<br>Leu Gln Ala Ser Leu Leu Lys Val Pro Tyr Phe Val Arg Val Gln Gly<br>        905                          910                        915 | 3092 |
| ctt ctc cgg atc tgc gcg cta gcg cgg aag ata gcc gga ggt cat tac<br>Leu Leu Arg Ile Cys Ala Leu Ala Arg Lys Ile Ala Gly Gly His Tyr<br>                      920                          925                        930 | 3140 |
| gtg caa atg gcc atc atc aag tta ggg gcg ctt act ggc acc tat gtg<br>Val Gln Met Ala Ile Ile Lys Leu Gly Ala Leu Thr Gly Thr Tyr Val<br>        935                          940                        945 | 3188 |
| tat aac cat ctc acc cct ctt cga gac tgg gcg cac aac ggc ctg cga<br>Tyr Asn His Leu Thr Pro Leu Arg Asp Trp Ala His Asn Gly Leu Arg<br>950                          955                        960                        965 | 3236 |
| gat ctg gcc gtg gct gtg gaa cca gtc gtc ttc tcc cga atg gag acc<br>Asp Leu Ala Val Ala Val Glu Pro Val Val Phe Ser Arg Met Glu Thr<br>                      970                          975                        980 | 3284 |
| aag ctc atc acg tgg ggg gca gat acc gcc gcg tgc ggt gac atc atc<br>Lys Leu Ile Thr Trp Gly Ala Asp Thr Ala Ala Cys Gly Asp Ile Ile<br>        985                          990                        995 | 3332 |
| aac ggc ttg ccc gtc tct gcc cgt agg ggc cag gag ata ctg ctt ggg<br>Asn Gly Leu Pro Val Ser Ala Arg Arg Gly Gln Glu Ile Leu Leu Gly<br>            1000                       1005                     1010 | 3380 |
| cca gcc gac gga atg gtc tcc aag ggg tgg agg ttg ctg gcg ccc atc<br>Pro Ala Asp Gly Met Val Ser Lys Gly Trp Arg Leu Leu Ala Pro Ile<br>  1015                        1020                       1025 | 3428 |
| acg gcg tac gcc cag cag acg aga ggc ctc cta ggg tgt ata atc acc<br>Thr Ala Tyr Ala Gln Gln Thr Arg Gly Leu Leu Gly Cys Ile Ile Thr<br>1030                      1035                     1040                     1045 | 3476 |
| agc ctg act ggc cgg gac aaa aac caa gtg gag ggt gag gtc cag atc<br>Ser Leu Thr Gly Arg Asp Lys Asn Gln Val Glu Gly Glu Val Gln Ile<br>            1050                       1055                     1060 | 3524 |
| gtg tca act gct acc caa acc ttc ctg gca acg tgc atc aat ggg gta<br>Val Ser Thr Ala Thr Gln Thr Phe Leu Ala Thr Cys Ile Asn Gly Val<br>  1065                        1070                       1075 | 3572 |
| tgc tgg act gtc tac cac ggg gcc gga acg agg acc atc gca tca ccc<br>Cys Trp Thr Val Tyr His Gly Ala Gly Thr Arg Thr Ile Ala Ser Pro<br>1080                      1085                     1090 | 3620 |
| aag ggt cct gtc atc cag atg tat acc aat gtg gac caa gac ctt gtg<br>Lys Gly Pro Val Ile Gln Met Tyr Thr Asn Val Asp Gln Asp Leu Val<br>    1095                     1100                     1105 | 3668 |
| ggc tgg ccc gct cct caa ggt tcc cgc tca ttg aca ccc tgt acc tgc | 3716 |

```
Gly Trp Pro Ala Pro Gln Gly Ser Arg Ser Leu Thr Pro Cys Thr Cys
1110                1115                1120                1125 ggc tcc tcg gac ctt tac ctg gtc acg agg cac gcc gat gtc att ccc      3764
Gly Ser Ser Asp Leu Tyr Leu Val Thr Arg His Ala Asp Val Ile Pro
            1130                1135                1140 gtg cgc cgg cga ggt gat agc agg ggt agc ctg ctt tcg ccc cgg ccc      3812
Val Arg Arg Arg Gly Asp Ser Arg Gly Ser Leu Leu Ser Pro Arg Pro
                1145                1150                1155 att tcc tac ttg aaa ggc tcc tcg ggg ggt ccg ctg ttg tgc ccc gcg      3860
Ile Ser Tyr Leu Lys Gly Ser Ser Gly Gly Pro Leu Leu Cys Pro Ala
        1160                1165                1170 gga cac gcc gtg ggc cta ttc agg gcc gcg gtg tgc acc cgt gga gtg      3908
Gly His Ala Val Gly Leu Phe Arg Ala Ala Val Cys Thr Arg Gly Val
    1175                1180                1185 gct aaa gcg gtg gac ttt atc cct gtg gag aac cta ggg aca acc atg      3956
Ala Lys Ala Val Asp Phe Ile Pro Val Glu Asn Leu Gly Thr Thr Met
1190                1195                1200                1205 aga tcc ccg gtg ttc acg gac aac tcc tct cca cca gca gtg ccc cag      4004
Arg Ser Pro Val Phe Thr Asp Asn Ser Ser Pro Pro Ala Val Pro Gln
            1210                1215                1220 agc ttc cag gtg gcc cac ctg cat gct ccc acc ggc agc ggt aag agc      4052
Ser Phe Gln Val Ala His Leu His Ala Pro Thr Gly Ser Gly Lys Ser
                1225                1230                1235 acc aag gtc ccg gct gcg tac gca gcc cag ggc tac aag gtg ttg gtg      4100
Thr Lys Val Pro Ala Ala Tyr Ala Ala Gln Gly Tyr Lys Val Leu Val
        1240                1245                1250 ctc aac ccc tct gtt gct gca acg ctg ggc ttt ggt gct tac atg tcc      4148
Leu Asn Pro Ser Val Ala Ala Thr Leu Gly Phe Gly Ala Tyr Met Ser
    1255                1260                1265 aag gcc cat ggg gtt gat cct aat atc agg acc ggg gtg aga aca att      4196
Lys Ala His Gly Val Asp Pro Asn Ile Arg Thr Gly Val Arg Thr Ile
1270                1275                1280                1285 acc act ggc agc ccc atc acg tac tcc acc tac ggc aag ttc ctt gcc      4244
Thr Thr Gly Ser Pro Ile Thr Tyr Ser Thr Tyr Gly Lys Phe Leu Ala
            1290                1295                1300 gac ggc ggg tgc tca gga ggt gct tat gac ata ata att tgt gac gag      4292
Asp Gly Gly Cys Ser Gly Gly Ala Tyr Asp Ile Ile Ile Cys Asp Glu
                1305                1310                1315 tgc cac tcc acg gat gcc aca tcc atc ttg ggc atc ggc act gtc ctt      4340
Cys His Ser Thr Asp Ala Thr Ser Ile Leu Gly Ile Gly Thr Val Leu
        1320                1325                1330 gac caa gca gag act gcg ggg gcg aga ctg gtt gtg ctc gcc act gct      4388
Asp Gln Ala Glu Thr Ala Gly Ala Arg Leu Val Val Leu Ala Thr Ala
    1335                1340                1345 acc cct ccg ggc tcc gtc act gtg tcc cat cct aac atc gag gag gtt      4436
Thr Pro Pro Gly Ser Val Thr Val Ser His Pro Asn Ile Glu Glu Val
1350                1355                1360                1365 gct ctg tcc acc acc gga gag atc ccc ttt tac ggc aag gct atc ccc      4484
Ala Leu Ser Thr Thr Gly Glu Ile Pro Phe Tyr Gly Lys Ala Ile Pro
            1370                1375                1380 ctc gag gtg atc aag ggg gga aga cat ctc atc ttc tgc cac tca aag      4532
Leu Glu Val Ile Lys Gly Gly Arg His Leu Ile Phe Cys His Ser Lys
                1385                1390                1395 aag aag tgc gac gag ctc gcc gcg aag ctg gtc gca ttg ggc atc aat      4580
Lys Lys Cys Asp Glu Leu Ala Ala Lys Leu Val Ala Leu Gly Ile Asn
        1400                1405                1410 gcc gtg gcc tac tac cgc ggt ctt gac gtg tct gtc atc ccg acc agc      4628
Ala Val Ala Tyr Tyr Arg Gly Leu Asp Val Ser Val Ile Pro Thr Ser
    1415                1420                1425
```

-continued

| | |
|---|---|
| ggc gat gtt gtc gtc gtg tcg acc gat gct ctc atg act ggc ttt acc<br>Gly Asp Val Val Val Ser Thr Asp Ala Leu Met Thr Gly Phe Thr<br>1430                   1435                 1440               1445 | 4676 |
| ggc gac ttc gac tct gtg ata gac tgc aac acg tgt gtc act cag aca<br>Gly Asp Phe Asp Ser Val Ile Asp Cys Asn Thr Cys Val Thr Gln Thr<br>1450                 1455                 1460 | 4724 |
| gtc gat ttc agc ctt gac cct acc ttt acc att gag aca acc acg ctc<br>Val Asp Phe Ser Leu Asp Pro Thr Phe Thr Ile Glu Thr Thr Thr Leu<br>1465                 1470                 1475 | 4772 |
| ccc cag gat gct gtc tcc agg act caa cgc cgg ggc agg act ggc agg<br>Pro Gln Asp Ala Val Ser Arg Thr Gln Arg Arg Gly Arg Thr Gly Arg<br>1480                 1485                 1490 | 4820 |
| ggg aag cca ggc atc tat aga ttt gtg gca ccg ggg gag cgc ccc tcc<br>Gly Lys Pro Gly Ile Tyr Arg Phe Val Ala Pro Gly Glu Arg Pro Ser<br>1495                 1500                 1505 | 4868 |
| ggc atg ttc gac tcg tcc gtc ctc tgt gag tgc tat gac gcg ggc tgt<br>Gly Met Phe Asp Ser Ser Val Leu Cys Glu Cys Tyr Asp Ala Gly Cys<br>1510                 1515                 1520               1525 | 4916 |
| gct tgg tat gag ctc acg ccc gcc gag act aca gtt agg cta cga gcg<br>Ala Trp Tyr Glu Leu Thr Pro Ala Glu Thr Thr Val Arg Leu Arg Ala<br>1530                 1535                 1540 | 4964 |
| tac atg aac acc ccg ggg ctt ccc gtg tgc cag gac cat ctt gaa ttt<br>Tyr Met Asn Thr Pro Gly Leu Pro Val Cys Gln Asp His Leu Glu Phe<br>1545                 1550                 1555 | 5012 |
| tgg gag ggc gtc ttt acg ggc ctc act cat ata gat gcc cac ttt tta<br>Trp Glu Gly Val Phe Thr Gly Leu Thr His Ile Asp Ala His Phe Leu<br>1560                 1565                 1570 | 5060 |
| tcc cag aca aag cag agt ggg gag aac ttt cct tac ctg gta gcg tac<br>Ser Gln Thr Lys Gln Ser Gly Glu Asn Phe Pro Tyr Leu Val Ala Tyr<br>1575                 1580                 1585 | 5108 |
| caa gcc acc gtg tgc gct agg gct caa gcc cct ccc cca tcg tgg gac<br>Gln Ala Thr Val Cys Ala Arg Ala Gln Ala Pro Pro Pro Ser Trp Asp<br>1590                 1595                 1600               1605 | 5156 |
| cag atg tgg aag tgt ttg atc cgc ctt aaa ccc acc ctc cat ggg cca<br>Gln Met Trp Lys Cys Leu Ile Arg Leu Lys Pro Thr Leu His Gly Pro<br>1610                 1615                 1620 | 5204 |
| aca ccc ctg cta tac aga ctg ggc gct gtt cag aat gaa gtc acc ctg<br>Thr Pro Leu Leu Tyr Arg Leu Gly Ala Val Gln Asn Glu Val Thr Leu<br>1625                 1630                 1635 | 5252 |
| acg cac cca atc acc aaa tac atc atg aca tgc atg tcg gcc gac ctg<br>Thr His Pro Ile Thr Lys Tyr Ile Met Thr Cys Met Ser Ala Asp Leu<br>1640                 1645                 1650 | 5300 |
| gag gtc gtc acg agc acc tgg gtg ctc gtt ggc ggc gtc ctg gct gct<br>Glu Val Val Thr Ser Thr Trp Val Leu Val Gly Gly Val Leu Ala Ala<br>1655                 1660                 1665 | 5348 |
| ctg gcc gcg tat tgc ctg tca aca ggc tgc gtg gtc ata gtg ggc agg<br>Leu Ala Ala Tyr Cys Leu Ser Thr Gly Cys Val Val Ile Val Gly Arg<br>1670                 1675                 1680               1685 | 5396 |
| atc gtc ttg tcc ggg aag ccg gca att ata cct gac agg gag gtt ctc<br>Ile Val Leu Ser Gly Lys Pro Ala Ile Ile Pro Asp Arg Glu Val Leu<br>1690                 1695                 1700 | 5444 |
| tac cag gag ttc gat gag atg gaa gag tgc tct cag cac tta ccg tac<br>Tyr Gln Glu Phe Asp Glu Met Glu Glu Cys Ser Gln His Leu Pro Tyr<br>1705                 1710                 1715 | 5492 |
| atc gag caa ggg atg atg ctc gct gag cag ttc aag cag aag gcc ctc<br>Ile Glu Gln Gly Met Met Leu Ala Glu Gln Phe Lys Gln Lys Ala Leu<br>1720                 1725                 1730 | 5540 |
| ggc ctc ctg cag acc gcg tcc cgc cat gca gag gtt atc acc cct gct<br>Gly Leu Leu Gln Thr Ala Ser Arg His Ala Glu Val Ile Thr Pro Ala<br>1735                 1740                 1745 | 5588 |

-continued

| | |
|---|---|
| gtc cag acc aac tgg cag aaa ctc gag gtc ttt tgg gcg aag cac atg<br>Val Gln Thr Asn Trp Gln Lys Leu Glu Val Phe Trp Ala Lys His Met<br>1750                  1755               1760               1765 | 5636 |
| tgg aat ttc atc agt ggg ata caa tac ttg gcg ggc ctg tca acg ctg<br>Trp Asn Phe Ile Ser Gly Ile Gln Tyr Leu Ala Gly Leu Ser Thr Leu<br>            1770               1775               1780 | 5684 |
| cct ggt aac ccc gcc att gct tca ttg atg gct ttt aca gct gcc gtc<br>Pro Gly Asn Pro Ala Ile Ala Ser Leu Met Ala Phe Thr Ala Ala Val<br>1785                  1790               1795 | 5732 |
| acc agc cca cta acc act ggc caa acc ctc ctc ttc aac ata ttg ggg<br>Thr Ser Pro Leu Thr Thr Gly Gln Thr Leu Leu Phe Asn Ile Leu Gly<br>            1800               1805               1810 | 5780 |
| ggg tgg gtg gct gcc cag ctc gcc gcc ccc ggt gcc gct act gcc ttt<br>Gly Trp Val Ala Ala Gln Leu Ala Ala Pro Gly Ala Ala Thr Ala Phe<br>    1815                  1820               1825 | 5828 |
| gtg ggt gct ggc cta gct ggc gcc gcc atc ggc agc gtt gga ctg ggg<br>Val Gly Ala Gly Leu Ala Gly Ala Ala Ile Gly Ser Val Gly Leu Gly<br>1830                  1835               1840               1845 | 5876 |
| aag gtc ctc gtg gac att ctt gca ggg tat ggc gcg ggc gtg gcg gga<br>Lys Val Leu Val Asp Ile Leu Ala Gly Tyr Gly Ala Gly Val Ala Gly<br>            1850               1855               1860 | 5924 |
| gct ctt gta gca ttc aag atc atg agc ggt gag gtc ccc tcc acg gag<br>Ala Leu Val Ala Phe Lys Ile Met Ser Gly Glu Val Pro Ser Thr Glu<br>    1865                  1870               1875 | 5972 |
| gac ctg gtc aat ctg ctg ccc gcc atc ctc tcg cct gga gcc ctt gta<br>Asp Leu Val Asn Leu Leu Pro Ala Ile Leu Ser Pro Gly Ala Leu Val<br>1880                  1885               1890 | 6020 |
| gtc ggt gtg gtc tgc gca gca ata ctg cgc cgg cac gtt ggc ccg ggc<br>Val Gly Val Val Cys Ala Ala Ile Leu Arg Arg His Val Gly Pro Gly<br>            1895               1900               1905 | 6068 |
| gag ggg gca gtg caa tgg atg aac cgg cta ata gcc ttc gcc tcc cgg<br>Glu Gly Ala Val Gln Trp Met Asn Arg Leu Ile Ala Phe Ala Ser Arg<br>1910                  1915               1920               1925 | 6116 |
| ggg aac cat gtt tcc ccc acg cac tac gtg ccg gag agc gat gca gcc<br>Gly Asn His Val Ser Pro Thr His Tyr Val Pro Glu Ser Asp Ala Ala<br>            1930               1935               1940 | 6164 |
| gcc cgc gtc act gcc ata ctc agc agc ctc act gta acc cag ctc ctg<br>Ala Arg Val Thr Ala Ile Leu Ser Ser Leu Thr Val Thr Gln Leu Leu<br>    1945                  1950               1955 | 6212 |
| agg cga ctg cat cag tgg ata agc tcg gag tgt acc act cca tgc tcc<br>Arg Arg Leu His Gln Trp Ile Ser Ser Glu Cys Thr Thr Pro Cys Ser<br>1960                  1965               1970 | 6260 |
| ggt tcc tgg cta agg gac atc tgg gac tgg ata tgc gag gtg ctg agc<br>Gly Ser Trp Leu Arg Asp Ile Trp Asp Trp Ile Cys Glu Val Leu Ser<br>1975                  1980               1985 | 6308 |
| gac ttt aag acc tgg ctg aaa gcc aag ctc atg cca caa ctg cct ggg<br>Asp Phe Lys Thr Trp Leu Lys Ala Lys Leu Met Pro Gln Leu Pro Gly<br>1990                  1995               2000               2005 | 6356 |
| att ccc ttt gtg tcc tgc cag cgc ggg tat agg ggg gtc tgg cga gga<br>Ile Pro Phe Val Ser Cys Gln Arg Gly Tyr Arg Gly Val Trp Arg Gly<br>            2010               2015               2020 | 6404 |
| gac ggc att atg cac act cgc tgc cac tgt gga gct gag atc act gga<br>Asp Gly Ile Met His Thr Arg Cys His Cys Gly Ala Glu Ile Thr Gly<br>    2025                  2030               2035 | 6452 |
| cat gtc aaa aac ggg acg atg agg atc gtc ggt cct agg acc tgc agg<br>His Val Lys Asn Gly Thr Met Arg Ile Val Gly Pro Arg Thr Cys Arg<br>2040                  2045               2050 | 6500 |
| aac atg tgg agt ggg acg ttc ccc att aac gcc tac acc acg ggc ccc<br>Asn Met Trp Ser Gly Thr Phe Pro Ile Asn Ala Tyr Thr Thr Gly Pro | 6548 |

-continued

```
                2055                2060                2065
       tgt act ccc ctt cct gcg ccg aac tat aag ttc gcg ctg tgg agg gtg    6596
       Cys Thr Pro Leu Pro Ala Pro Asn Tyr Lys Phe Ala Leu Trp Arg Val
       2070                2075                2080                2085 tct gca gag gaa tac gtg gag ata agg cgg gtg ggg gac ttc cac tac    6644
       Ser Ala Glu Glu Tyr Val Glu Ile Arg Arg Val Gly Asp Phe His Tyr
                       2090                2095                2100 gta tcg ggt atg act act gac aat ctt aaa tgc ccg tgc cag atc cca    6692
       Val Ser Gly Met Thr Thr Asp Asn Leu Lys Cys Pro Cys Gln Ile Pro
               2105                2110                2115 tcg ccc gaa ttt ttc aca gaa ttg gac ggg gtg cgc cta cac agg ttt    6740
       Ser Pro Glu Phe Phe Thr Glu Leu Asp Gly Val Arg Leu His Arg Phe
       2120                2125                2130 gcg ccc cct tgc aag ccc ttg ctg cgg gag gag gta tca ttc aga gta    6788
       Ala Pro Pro Cys Lys Pro Leu Leu Arg Glu Glu Val Ser Phe Arg Val
                       2135                2140                2145 gga ctc cac gag tac ccg gtg ggg tcg caa tta cct tgc gag ccc gaa    6836
       Gly Leu His Glu Tyr Pro Val Gly Ser Gln Leu Pro Cys Glu Pro Glu
       2150                2155                2160                2165 ccg gac gta gcc gtg ttg acg tcc atg ctc act gat ccc tcc cat ata    6884
       Pro Asp Val Ala Val Leu Thr Ser Met Leu Thr Asp Pro Ser His Ile
                       2170                2175                2180 aca gca gag gcg gcc ggg aga agg ttg gcg aga ggg tca ccc cct tct    6932
       Thr Ala Glu Ala Ala Gly Arg Arg Leu Ala Arg Gly Ser Pro Pro Ser
               2185                2190                2195 atg gcc agc tcc tcg gct agc cag ctg tcc gct cca tct ctc aag gca    6980
       Met Ala Ser Ser Ser Ala Ser Gln Leu Ser Ala Pro Ser Leu Lys Ala
       2200                2205                2210 act tgc acc gcc aac cat gac tcc cct gac gcc gag ctc ata gag gct    7028
       Thr Cys Thr Ala Asn His Asp Ser Pro Asp Ala Glu Leu Ile Glu Ala
                       2215                2220                2225 aac ctc ctg tgg agg cag gag atg ggc ggc aac atc acc agg gtt gag    7076
       Asn Leu Leu Trp Arg Gln Glu Met Gly Gly Asn Ile Thr Arg Val Glu
       2230                2235                2240                2245 tca gag aac aaa gtg gtg att ctg gac tcc ttc gat ccg ctt gtg gca    7124
       Ser Glu Asn Lys Val Val Ile Leu Asp Ser Phe Asp Pro Leu Val Ala
                       2250                2255                2260 gag gag gat gag cgg gag gtc tcc gta cct gca gaa att ctg cgg aag    7172
       Glu Glu Asp Glu Arg Glu Val Ser Val Pro Ala Glu Ile Leu Arg Lys
               2265                2270                2275 tct cgg aga ttc gcc cgg gcc ctg ccc gtc tgg gcg cgg ccg gac tac    7220
       Ser Arg Arg Phe Ala Arg Ala Leu Pro Val Trp Ala Arg Pro Asp Tyr
       2280                2285                2290 aac ccc ccg cta gta gag acg tgg aaa aag cct gac tac gaa cca cct    7268
       Asn Pro Pro Leu Val Glu Thr Trp Lys Lys Pro Asp Tyr Glu Pro Pro
                       2295                2300                2305 gtg gtc cat ggc tgc ccg cta cca cct cca cgg tcc cct cct gtg cct    7316
       Val Val His Gly Cys Pro Leu Pro Pro Pro Arg Ser Pro Pro Val Pro
       2310                2315                2320                2325 ccg cct cgg aaa aag cgt acg gtg gtc ctc acc gaa tca acc cta tct    7364
       Pro Pro Arg Lys Lys Arg Thr Val Val Leu Thr Glu Ser Thr Leu Ser
                       2330                2335                2340 act gcc ttg gcc gag ctt gcc acc aaa agt ttt ggc agc tcc tca act    7412
       Thr Ala Leu Ala Glu Leu Ala Thr Lys Ser Phe Gly Ser Ser Ser Thr
               2345                2350                2355 tcc ggc att acg ggc gac aat acg aca aca tcc tct gag ccc gcc cct    7460
       Ser Gly Ile Thr Gly Asp Asn Thr Thr Thr Ser Ser Glu Pro Ala Pro
       2360                2365                2370 tct ggc tgc ccc ccc gac tcc gac gtt gag tcc tat tct tcc atg ccc    7508
```

```
Ser Gly Cys Pro Pro Asp Ser Asp Val Glu Ser Tyr Ser Ser Met Pro
        2375                2380                2385 ccc ctg gag ggg gag cct ggg gat ccg gat ctc agc gac ggg tca tgg         7556
Pro Leu Glu Gly Glu Pro Gly Asp Pro Asp Leu Ser Asp Gly Ser Trp
2390            2395                2400                2405 tcg acg gtc agt agt ggg gcc gac acg gaa gat gtc gtg tgc tgc tca         7604
Ser Thr Val Ser Ser Gly Ala Asp Thr Glu Asp Val Val Cys Cys Ser
                2410                2415                2420 atg tct tat tcc tgg aca ggc gca ctc gtc acc ccg tgc gct gcg gaa         7652
Met Ser Tyr Ser Trp Thr Gly Ala Leu Val Thr Pro Cys Ala Ala Glu
        2425                2430                2435 gaa caa aaa ctg ccc atc aac gca ctg agc aac tcg ttg cta cgc cat         7700
Glu Gln Lys Leu Pro Ile Asn Ala Leu Ser Asn Ser Leu Leu Arg His
    2440                2445                2450 cac aat ctg gtg tat tcc acc act tca cgc agt gct tgc caa agg cag         7748
His Asn Leu Val Tyr Ser Thr Thr Ser Arg Ser Ala Cys Gln Arg Gln
2455                2460                2465 aag aaa gtc aca ttt gac aga ctg caa gtt ctg gac agc cat tac cag         7796
Lys Lys Val Thr Phe Asp Arg Leu Gln Val Leu Asp Ser His Tyr Gln
2470            2475                2480                2485 gac gtg ctc aag gag gtc aaa gca gcg gcg tca aaa gtg aag gct aac         7844
Asp Val Leu Lys Glu Val Lys Ala Ala Ala Ser Lys Val Lys Ala Asn
                2490                2495                2500 ttg cta tcc gta gag gaa gct tgc agc ctg acg ccc cca cat tca gcc         7892
Leu Leu Ser Val Glu Glu Ala Cys Ser Leu Thr Pro Pro His Ser Ala
        2505                2510                2515 aaa tcc aag ttt ggc tat ggg gca aaa gac gtc cgt tgc cat gcc aga         7940
Lys Ser Lys Phe Gly Tyr Gly Ala Lys Asp Val Arg Cys His Ala Arg
    2520                2525                2530 aag gcc gta gcc cac atc aac tcc gtg tgg aaa gac ctt ctg gaa gac         7988
Lys Ala Val Ala His Ile Asn Ser Val Trp Lys Asp Leu Leu Glu Asp
2535                2540                2545 agt gta aca cca ata gac act acc atc atg gcc aag aac gag gtt ttc         8036
Ser Val Thr Pro Ile Asp Thr Thr Ile Met Ala Lys Asn Glu Val Phe
2550            2555                2560                2565 tgc gtt cag cct gag aag ggg ggt cgt aag cca gct cgt ctc atc gtg         8084
Cys Val Gln Pro Glu Lys Gly Gly Arg Lys Pro Ala Arg Leu Ile Val
                2570                2575                2580 ttc ccc gac ctg ggc gtg cgc gtg tgc gag aag atg gcc ctg tac gac         8132
Phe Pro Asp Leu Gly Val Arg Val Cys Glu Lys Met Ala Leu Tyr Asp
        2585                2590                2595 gtg gtt agc aag ctc ccc ctg gcc gtg atg gga agc tcc tac gga ttc         8180
Val Val Ser Lys Leu Pro Leu Ala Val Met Gly Ser Ser Tyr Gly Phe
    2600                2605                2610 caa tac tca cca gga cag cgg gtt gaa ttc ctc gtg caa gcg tgg aag         8228
Gln Tyr Ser Pro Gly Gln Arg Val Glu Phe Leu Val Gln Ala Trp Lys
2615                2620                2625 tcc aag aag acc ccg atg ggg ttc tcg tat gat acc cgc tgt ttt gac         8276
Ser Lys Lys Thr Pro Met Gly Phe Ser Tyr Asp Thr Arg Cys Phe Asp
2630            2635                2640                2645 tcc aca gtc act gag agc gac atc cgt acg gag gag gca att tac caa         8324
Ser Thr Val Thr Glu Ser Asp Ile Arg Thr Glu Glu Ala Ile Tyr Gln
                2650                2655                2660 tgt tgt gac ctg gac ccc caa gcc cgc gtg gcc atc aag tcc ctc act         8372
Cys Cys Asp Leu Asp Pro Gln Ala Arg Val Ala Ile Lys Ser Leu Thr
        2665                2670                2675 gag agg ctt tat gtt ggg ggc cct ctt acc aat tca agg ggg gaa aac         8420
Glu Arg Leu Tyr Val Gly Gly Pro Leu Thr Asn Ser Arg Gly Glu Asn
    2680                2685                2690
```

-continued

| | |
|---|---|
| tgc ggc tac cgc agg tgc cgc gcg agc ggc gta ctg aca act agc tgt<br>Cys Gly Tyr Arg Arg Cys Arg Ala Ser Gly Val Leu Thr Thr Ser Cys<br>2695                                  2700                             2705 | 8468 |
| ggt aac acc ctc act tgc tac atc aag gcc cgg gca gcc tgt cga gcc<br>Gly Asn Thr Leu Thr Cys Tyr Ile Lys Ala Arg Ala Ala Cys Arg Ala<br>2710                            2715                            2720                           2725 | 8516 |
| gca ggg ctc cag gac tgc acc atg ctc gtg tgt ggc gac gac tta gtc<br>Ala Gly Leu Gln Asp Cys Thr Met Leu Val Cys Gly Asp Asp Leu Val<br>                         2730                            2735                            2740 | 8564 |
| gtt atc tgt gaa agt gcg ggg gtc cag gag gac gcg gcg agc ctg aga<br>Val Ile Cys Glu Ser Ala Gly Val Gln Glu Asp Ala Ala Ser Leu Arg<br>2745                                  2750                              2755 | 8612 |
| gcc ttc acg gag gct atg acc agg tac tcc gcc ccc ccc ggg gac ccc<br>Ala Phe Thr Glu Ala Met Thr Arg Tyr Ser Ala Pro Pro Gly Asp Pro<br>                         2760                            2765                            2770 | 8660 |
| cca caa cca gaa tac gac ttg gag ctt ata aca tca tgc tcc tcc aac<br>Pro Gln Pro Glu Tyr Asp Leu Glu Leu Ile Thr Ser Cys Ser Ser Asn<br>2775                                  2780                              2785 | 8708 |
| gtg tca gtc gcc cac gac ggc gct gga aag agg gtc tac tac ctt acc<br>Val Ser Val Ala His Asp Gly Ala Gly Lys Arg Val Tyr Tyr Leu Thr<br>2790                                  2795                              2800                           2805 | 8756 |
| cgt gac cct aca acc ccc ctc gcg aga gcc gcg tgg gag aca gca aga<br>Arg Asp Pro Thr Thr Pro Leu Ala Arg Ala Ala Trp Glu Thr Ala Arg<br>                         2810                            2815                            2820 | 8804 |
| cac act cca gtc aat tcc tgg cta ggc aac ata atc atg ttt gcc ccc<br>His Thr Pro Val Asn Ser Trp Leu Gly Asn Ile Ile Met Phe Ala Pro<br>2825                                  2830                              2835 | 8852 |
| aca ctg tgg gcg agg atg ata ctg atg acc cat ttc ttt agc gtc ctc<br>Thr Leu Trp Ala Arg Met Ile Leu Met Thr His Phe Phe Ser Val Leu<br>2840                                  2845                              2850 | 8900 |
| ata gcc agg gat cag ctt gaa cag gct ctt aac tgt gag atc tac gga<br>Ile Ala Arg Asp Gln Leu Glu Gln Ala Leu Asn Cys Glu Ile Tyr Gly<br>2855                                  2860                              2865 | 8948 |
| gcc tgc tac tcc ata gaa cca ctg gat cta cct cca atc att caa aga<br>Ala Cys Tyr Ser Ile Glu Pro Leu Asp Leu Pro Pro Ile Ile Gln Arg<br>2870                                  2875                              2880                           2885 | 8996 |
| ctc cat ggc ctc agc gca ttt tca ctc cac agt tac tct cca ggt gaa<br>Leu His Gly Leu Ser Ala Phe Ser Leu His Ser Tyr Ser Pro Gly Glu<br>                         2890                            2895                            2900 | 9044 |
| atc aat agg gtg gcc gca tgc ctc aga aaa ctt ggg gtc ccg ccc ttg<br>Ile Asn Arg Val Ala Ala Cys Leu Arg Lys Leu Gly Val Pro Pro Leu<br>2905                                  2910                              2915 | 9092 |
| cga gct tgg aga cac cgg gcc cgg agc gtc cgc gct agg ctt ctg tcc<br>Arg Ala Trp Arg His Arg Ala Arg Ser Val Arg Ala Arg Leu Leu Ser<br>2920                                  2925                              2930 | 9140 |
| aga gga ggc agg gct gcc ata tgt ggc aag tac ctc ttc aac tgg gca<br>Arg Gly Gly Arg Ala Ala Ile Cys Gly Lys Tyr Leu Phe Asn Trp Ala<br>2935                                  2940                              2945 | 9188 |
| gta aga aca aag ctc aaa ctc act cca ata gcg gcc gct ggc cgg ctg<br>Val Arg Thr Lys Leu Lys Leu Thr Pro Ile Ala Ala Ala Gly Arg Leu<br>2950                                  2955                              2960                           2965 | 9236 |
| gac ttg tcc ggt tgg ttc acg gct ggc tac agc ggg gga gac att tat<br>Asp Leu Ser Gly Trp Phe Thr Ala Gly Tyr Ser Gly Gly Asp Ile Tyr<br>                         2970                            2975                            2980 | 9284 |
| cac agc gtg tct cat gcc cgg ccc cgc tgg ttc tgg ttt tgc cta ctc<br>His Ser Val Ser His Ala Arg Pro Arg Trp Phe Trp Phe Cys Leu Leu<br>                         2985                            2990                            2995 | 9332 |
| ctg ctc gct gca ggg gta ggc atc tac ctc ctc ccc aac cga tga<br>Leu Leu Ala Ala Gly Val Gly Ile Tyr Leu Leu Pro Asn Arg<br>3000                                  3005                              3010 | 9377 |

-continued

```
aggttggggt aaacactccg gcctcttaag ccatttcctg tttttttttt tttttttttt    9437 tttttttttct tttttttttt ctttccttttc cttcttttttt tcctttctttt ttcccttctt   9497 taatggtggc tccatcttag ccctagtcac ggctagctgt gaaaggtccg tgagccgcat    9557
gactgcagag agtgctgata ctggcctctc tgcagatcat gt                       9599
```

<210> SEQ ID NO 14
<211> LENGTH: 3011
<212> TYPE: PRT
<213> ORGANISM: Hepatitis C virus

<400> SEQUENCE: 14

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335
```

-continued

```
Leu Leu Arg Ile Pro Gln Ala Ile Met Asp Met Ile Ala Gly Ala His
            340                 345                 350
Trp Gly Val Leu Ala Gly Ile Ala Tyr Phe Ser Met Val Gly Asn Trp
            355                 360                 365
Ala Lys Val Leu Val Val Leu Leu Phe Ala Gly Val Asp Ala Glu
            370                 375                 380
Thr His Val Thr Gly Gly Asn Ala Gly Arg Thr Thr Ala Gly Leu Val
385                 390                 395                 400
Gly Leu Leu Thr Pro Gly Ala Lys Gln Asn Ile Gln Leu Ile Asn Thr
                405                 410                 415
Asn Gly Ser Trp His Ile Asn Ser Thr Ala Leu Asn Cys Asn Glu Ser
                420                 425                 430
Leu Asn Thr Gly Trp Leu Ala Gly Leu Phe Tyr Gln His Lys Phe Asn
            435                 440                 445
Ser Ser Gly Cys Pro Glu Arg Leu Ala Ser Cys Arg Arg Leu Thr Asp
450                 455                 460
Phe Ala Gln Gly Trp Gly Pro Ile Ser Tyr Ala Asn Gly Ser Gly Leu
465                 470                 475                 480
Asp Glu Arg Pro Tyr Cys Trp His Tyr Pro Arg Pro Cys Gly Ile
                485                 490                 495
Val Pro Ala Lys Ser Val Cys Gly Pro Val Tyr Cys Phe Thr Pro Ser
                500                 505                 510
Pro Val Val Val Gly Thr Thr Asp Arg Ser Gly Ala Pro Thr Tyr Ser
            515                 520                 525
Trp Gly Ala Asn Asp Thr Asp Val Phe Val Leu Asn Asn Thr Arg Pro
            530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Val Gly Asn
                565                 570                 575
Asn Thr Leu Leu Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Met
            595                 600                 605
Val Asp Tyr Pro Tyr Arg Leu Trp His Tyr Pro Cys Thr Ile Asn Tyr
            610                 615                 620
Thr Ile Phe Lys Val Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Gln Trp
                660                 665                 670
Gln Val Leu Pro Cys Ser Phe Thr Thr Leu Pro Ala Leu Ser Thr Gly
            675                 680                 685
Leu Ile His Leu His Gln Asn Ile Val Asp Val Gln Tyr Leu Tyr Gly
            690                 695                 700
Val Gly Ser Ser Ile Ala Ser Trp Ala Ile Lys Trp Glu Tyr Val Val
705                 710                 715                 720
Leu Leu Phe Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
                740                 745                 750
```

```
Ile Leu Asn Ala Ala Ser Leu Ala Gly Thr His Gly Leu Val Ser Phe
            755                 760                 765
Leu Val Phe Phe Cys Phe Ala Trp Tyr Leu Lys Gly Arg Trp Val Pro
        770                 775                 780
Gly Ala Val Tyr Ala Leu Tyr Gly Met Trp Pro Leu Leu Leu Leu Leu
785                 790                 795                 800
Leu Ala Leu Pro Gln Arg Ala Tyr Ala Leu Asp Thr Glu Val Ala Ala
                805                 810                 815
Ser Cys Gly Gly Val Leu Val Gly Leu Met Ala Leu Thr Leu Ser
            820                 825                 830
Pro Tyr Tyr Lys Arg Tyr Ile Ser Trp Cys Met Trp Trp Leu Gln Tyr
        835                 840                 845
Phe Leu Thr Arg Val Glu Ala Gln Leu His Val Trp Val Pro Pro Leu
850                 855                 860
Asn Val Arg Gly Gly Arg Asp Ala Val Ile Leu Leu Met Cys Val Val
865                 870                 875                 880
His Pro Thr Leu Val Phe Asp Ile Thr Lys Leu Leu Leu Ala Ile Phe
                885                 890                 895
Gly Pro Leu Trp Ile Leu Gln Ala Ser Leu Leu Lys Val Pro Tyr Phe
            900                 905                 910
Val Arg Val Gln Gly Leu Leu Arg Ile Cys Ala Leu Ala Arg Lys Ile
        915                 920                 925
Ala Gly Gly His Tyr Val Gln Met Ala Ile Ile Lys Leu Gly Ala Leu
    930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Val Phe
                965                 970                 975
Ser Arg Met Glu Thr Lys Leu Ile Thr Trp Gly Ala Asp Thr Ala Ala
            980                 985                 990
Cys Gly Asp Ile Ile Asn Gly Leu Pro Val Ser Ala Arg Arg Gly Gln
        995                 1000                1005
Glu Ile Leu Leu Gly Pro Ala Asp Gly Met Val Ser Lys Gly Trp Arg
    1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Thr Gln Thr Phe Leu Ala Thr
            1060                1065                1070
Cys Ile Asn Gly Val Cys Trp Thr Val Tyr His Gly Ala Gly Thr Arg
        1075                1080                1085
Thr Ile Ala Ser Pro Lys Gly Pro Val Ile Gln Met Tyr Thr Asn Val
    1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
            1140                1145                1150
Leu Ser Pro Arg Pro Ile Ser Tyr Leu Lys Gly Ser Ser Gly Gly Pro
        1155                1160                1165
Leu Leu Cys Pro Ala Gly His Ala Val Gly Leu Phe Arg Ala Ala Val
```

```
                      1170                1175                1180
Cys Thr Arg Gly Val Ala Lys Ala Val Asp Phe Ile Pro Val Glu Asn
1185                1190                1195                1200

Leu Gly Thr Thr Met Arg Ser Pro Val Phe Thr Asp Asn Ser Ser Pro
                      1205                1210                1215

Pro Ala Val Pro Gln Ser Phe Gln Val Ala His Leu His Ala Pro Thr
                1220                1225                1230

Gly Ser Gly Lys Ser Thr Lys Val Pro Ala Ala Tyr Ala Ala Gln Gly
          1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
                      1285                1290                1295

Gly Lys Phe Leu Ala Asp Gly Gly Cys Ser Gly Gly Ala Tyr Asp Ile
                1300                1305                1310

Ile Ile Cys Asp Glu Cys His Ser Thr Asp Ala Thr Ser Ile Leu Gly
          1315                1320                1325

Ile Gly Thr Val Leu Asp Gln Ala Glu Thr Ala Gly Ala Arg Leu Val
    1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
                      1365                1370                1375

Gly Lys Ala Ile Pro Leu Glu Val Ile Lys Gly Gly Arg His Leu Ile
                1380                1385                1390

Phe Cys His Ser Lys Lys Lys Cys Asp Glu Leu Ala Ala Lys Leu Val
          1395                1400                1405

Ala Leu Gly Ile Asn Ala Val Ala Tyr Tyr Arg Gly Leu Asp Val Ser
    1410                1415                1420

Val Ile Pro Thr Ser Gly Asp Val Val Val Ser Thr Asp Ala Leu
1425                1430                1435                1440

Met Thr Gly Phe Thr Gly Asp Phe Asp Ser Val Ile Asp Cys Asn Thr
                      1445                1450                1455

Cys Val Thr Gln Thr Val Asp Phe Ser Leu Asp Pro Thr Phe Thr Ile
                1460                1465                1470

Glu Thr Thr Thr Leu Pro Gln Asp Ala Val Ser Arg Thr Gln Arg Arg
          1475                1480                1485

Gly Arg Thr Gly Arg Gly Lys Pro Gly Ile Tyr Arg Phe Val Ala Pro
    1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
                      1525                1530                1535

Val Arg Leu Arg Ala Tyr Met Asn Thr Pro Gly Leu Pro Val Cys Gln
                1540                1545                1550

Asp His Leu Glu Phe Trp Glu Gly Val Phe Thr Gly Leu Thr His Ile
          1555                1560                1565

Asp Ala His Phe Leu Ser Gln Thr Lys Gln Ser Gly Glu Asn Phe Pro
    1570                1575                1580
```

```
Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Thr Cys
        1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
            1685                1690                1695

Asp Arg Glu Val Leu Tyr Gln Glu Phe Asp Glu Met Glu Glu Cys Ser
            1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg His Ala Glu
        1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Gly Gln Thr Leu Leu
        1795                1800                1805

Phe Asn Ile Leu Gly Gly Trp Val Ala Ala Gln Leu Ala Ala Pro Gly
    1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
            1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935

Glu Ser Asp Ala Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
        1955                1960                1965

Thr Thr Pro Cys Ser Gly Ser Trp Leu Arg Asp Ile Trp Asp Trp Ile
    1970                1975                1980
```

-continued

```
Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
        2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
        2035                2040                2045

Pro Arg Thr Cys Arg Asn Met Trp Ser Gly Thr Phe Pro Ile Asn Ala
        2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
            2085                2090                2095

Gly Asp Phe His Tyr Val Ser Gly Met Thr Thr Asp Asn Leu Lys Cys
        2100                2105                2110

Pro Cys Gln Ile Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
    2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
        2180                2185                2190

Gly Ser Pro Pro Ser Met Ala Ser Ser Ser Ala Ser Gln Leu Ser Ala
        2195                2200                2205

Pro Ser Leu Lys Ala Thr Cys Thr Ala Asn His Asp Ser Pro Asp Ala
    2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Asp Pro Leu Val Ala Glu Glu Asp Glu Arg Glu Val Ser Val Pro Ala
        2260                2265                2270

Glu Ile Leu Arg Lys Ser Arg Arg Phe Ala Arg Ala Leu Pro Val Trp
        2275                2280                2285

Ala Arg Pro Asp Tyr Asn Pro Pro Leu Val Glu Thr Trp Lys Lys Pro
    2290                2295                2300

Asp Tyr Glu Pro Pro Val Val His Gly Cys Pro Leu Pro Pro Pro Arg
2305                2310                2315                2320

Ser Pro Pro Val Pro Pro Pro Arg Lys Lys Arg Thr Val Val Leu Thr
            2325                2330                2335

Glu Ser Thr Leu Ser Thr Ala Leu Ala Glu Leu Ala Thr Lys Ser Phe
        2340                2345                2350

Gly Ser Ser Ser Thr Ser Gly Ile Thr Gly Asp Asn Thr Thr Thr Ser
        2355                2360                2365

Ser Glu Pro Ala Pro Ser Gly Cys Pro Pro Asp Ser Asp Val Glu Ser
    2370                2375                2380

Tyr Ser Ser Met Pro Pro Leu Glu Gly Glu Pro Gly Asp Pro Asp Leu
2385                2390                2395                2400
```

-continued

```
Ser Asp Gly Ser Trp Ser Thr Val Ser Ser Gly Ala Asp Thr Glu Asp
            2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
            2435                2440                2445

Ser Leu Leu Arg His His Asn Leu Val Tyr Ser Thr Thr Ser Arg Ser
            2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
            2485                2490                2495

Lys Val Lys Ala Asn Leu Leu Ser Val Glu Glu Ala Cys Ser Leu Thr
            2500                2505                2510

Pro Pro His Ser Ala Lys Ser Lys Phe Gly Tyr Gly Ala Lys Asp Val
            2515                2520                2525

Arg Cys His Ala Arg Lys Ala Val Ala His Ile Asn Ser Val Trp Lys
            2530                2535                2540

Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
            2565                2570                2575

Ala Arg Leu Ile Val Phe Pro Asp Leu Gly Val Arg Val Cys Glu Lys
            2580                2585                2590

Met Ala Leu Tyr Asp Val Val Ser Lys Leu Pro Leu Ala Val Met Gly
            2595                2600                2605

Ser Ser Tyr Gly Phe Gln Tyr Ser Pro Gly Gln Arg Val Glu Phe Leu
            2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
            2675                2680                2685

Ser Arg Gly Glu Asn Cys Gly Tyr Arg Arg Cys Arg Ala Ser Gly Val
            2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815
```

```
Trp Glu Thr Ala Arg His Thr Pro Val Asn Ser Trp Leu Gly Asn Ile
        2820                2825                2830

Ile Met Phe Ala Pro Thr Leu Trp Ala Arg Met Ile Leu Met Thr His
    2835                2840                2845

Phe Phe Ser Val Leu Ile Ala Arg Asp Gln Leu Glu Gln Ala Leu Asn
2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
        2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ser Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
        2980                2985                2990

Trp Phe Cys Leu Leu Leu Leu Ala Ala Gly Val Gly Ile Tyr Leu Leu
        2995                3000                3005

Pro Asn Arg
    3010

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
gaaggaggga ggtttgaagg a                                             21

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
ccagttccgg gcaagaact                                                19

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 17
aattcggccc tgcaggccac aacagtc                                       27
```

3' SEQUENCE OF THE GB VIRUS B (GBV-B) GENOME

The present application claims the benefit of U.S. Provisional Application Ser. No. 60/137,665 filed on Jun. 4, 1999. The entire text of the above-referenced disclosure is herein incorporated by reference.

BACKGROUND OF THE INVENTION

A. Field of the Invention

The present invention relates generally to the fields of biochemistry, molecular biology, and virology. More particularly, it relates to the identification of 259 nucleotides of previously unrecognized sequence located at the 3' end of the GB virus B (GBV-B) genome.

B. Description of Related Art

Chronic hepatitis C is a major threat to the public health. Serologic surveys suggest that as many as 3.9 million Americans are chronically infected with the responsible virus, hepatitis C virus (HCV) (Alter, 1997). These individuals are at increased risk of developing progressive hepatic fibrosis leading to cirrhosis and loss of hepatocellular function, as well as hepatocellular carcinoma. The course of chronic hepatitis C is typically lengthy, often extending over decades, with insidious clinical progression usually occurring in the absence of symptoms. Nonetheless, liver disease due to HCV results in the death of 8,000-10,000 Americans annually, and chronic hepatitis C is the most common cause of liver transplantation within the U.S.

Therefore, HCV is a major public health problem. However, therapy for chronic hepatitis C is problematic. Recombinant interferon-α is approved for treatment of chronic hepatitis C (Consensus Development Panel, 1997). The benefit of interferon-α results primarily from its antiviral properties and its ability to inhibit production of virus by infected hepatocytes (Neumann et al., 1998). Nonetheless, even under optimal therapeutic regimens, the majority of patients with chronic hepatitis C fail to eliminate the virus or resolve their liver disease. Treatment failures are especially common in persons infected with genotype 1 HCV, unfortunately the most prevalent genotype in the U.S. Thus, there is an urgent need to better understand the virus and develop better treatment. Unfortunately, technical difficulties in working with HCV have made it necessary to use infectious surrogate viruses in efforts to develop treatments and vaccines for HCV.

Scientists' efforts to better understand HCV and to develop new drugs for treatment of hepatitis C have been stymied by two overwhelming technical deficiencies: first, the nonexistence of a high permissive cell line that supports replication of the virus and second, the absence of a permissive animal species other than chimpanzees, which are endangered and therefore available on a limited basis.

Presently, those who are working on HCV treatment and prevention are employing an infectious chimeric virus of sindbis and HCV and/or an infectious clone of pestiviruses as surrogate virus models in HCV drug discovery efforts, due to the above technical difficulties of working with HCV. Alternatively, they are using isolated proteins or RNA segments of HCV for biochemical and structural studies. This approach precludes functional studies of virus replication and its inhibition.

GBV-B is a hepatotropic flavivirus that has a unique phylogenetic relationship to human HCV and strong potential to serve as a surrogate virus in drug discovery efforts related to hepatitis C antiviral drug development. GBV-B causes acute hepatitis in experimentally infected tamarins (Simons et al., 1995; Schlauder et al., 1995; Karayiannis et al., 1989) and can serve as a surrogate virus for HCV in drug discovery efforts (due to technical difficulties in working with HCV). GBV-B virus is much closer in sequence and biological properties than the above-described models. It will be easier to make biologically relevant chimeras between HCV and GBV-B than by using more distantly related viruses. GBV-B is hepatotropic (as is HCV), whereas the viruses used in these competing technologies are not. In view of the above, an infectious clone of GBV-B would be useful to those working on HCV treatment and prevention.

Unfortunately, the use of GBV-B as a surrogate or model for HCV has not been possible in the past, because no infectious molecular clone of GBV-B virus genome could be prepared. It is now known that this obstacle was encountered because the GBV-B genome was believed to be 259 nucleotides shorter than its actual length (Muerhoff et al., 1995; Simons et al., 1995). Others, previous to the inventors, had failed to realize that the 3' sequence of GBV-B was missing from the prior sequences. Without this 3' sequence, it is not possible to prepare an infectious GBV-B molecular clone.

SUMMARY OF THE INVENTION

As discussed above, an infectious molecular clone of GBV-B would be very useful for the development of HCV preventative and therapeutic treatments. The construction of an infectious molecular clone of this virus will require the newly determined 3' sequence to be included in order for the clone to be viable. The inventors have elucidated the previously unrecognized 3' terminal sequence of GBV-B (SEQ ID NO:1). This sequence has been reproducibly recovered from tamarin serum containing GBV-B RNA, in RT-PCR protocols using several different primer sets, and as a fusion with previously reported 5' GBV-B sequences.

The newly identified 3' sequence is not included in published reports of the GBV-B sequence, nor described in patents relating to the original identification of the viral sequence (see U.S. Pat. No. 5,807,670 and references therein).

The invention has utility in that the inclusion of the sequence will be necessary for construction of an infectious molecular GBV-B clone. Such clones clearly have the potential to be constructed as chimeras including relevant hepatitis C virus sequences in lieu of the homologous GBV-B sequence, providing unique tools for drug discovery efforts. A full-length molecular clone of GBV-was constructed, as described in later sections of this specification.

GBV-B can be used as a model for HCV, and the GBV-B genome can be used as the acceptor molecule in the construction of chimeric viral RNAs containing sequences of both HCV and GBV-B. Such studies will allow one to investigate the mechanisms for the different biological properties of these viruses and to discover and investigate potential inhibitors of specific HCV activities (e.g., proteinase) required for HCV replication. However, all this work is dependent upon construction of an infectious clone of GBV-B, which is itself dependent on the incorporation of the correct 3' terminal nucleotide sequence within this clone. GBV-B has unique advantages over HCV in terms of its ability to replicate and cause liver disease in tamarins, which present fewer restrictions to research than chimpanzees, the only nonhuman primate species known to be permissive for HCV.

An infectious molecular clone of GBV-B is expected to have utility in liver-specific gene expression or in gene therapy. This application might be enhanced by the inclusion of HCV genomic sequence in the form of a GBV-B/HCV chimera. Further, an infectious GBV-B/HCV chimera expressing HCV envelope proteins can have utility as a vaccine immunogen for hepatitis C.

A full-length cDNA copy of the GBV-B genome was constructed to contain the newly identified 3' terminal sequences. RNA transcribed from this cDNA copy of the genome would be infectious when inoculated into the liver of a GBV-B permissive tamarin, giving rise to rescued GBV-B virus particles. A chimeric molecule would then be constructed from this infectious GBV-B clone in which the HCV NS3 proteinase or proteinase/helicase sequence (or other relevant HCV sequences of interest in drug discovery efforts) would be placed in frame in lieu of the homologous GBV-B sequence, and this chimeric cDNA would be used to generate infectious GBV-B/HCV chimeric viruses by intrahepatic inoculation of synthetic RNA in tamarins. Published studies indicate that the GBV-B and HCV proteinases have closely related substrate recognition and cleavage properties, making such chimeras highly likely to be viable. These newly generated chimeric GBV-B/HCV viruses could be used in preclinical testing of candidate HCV NS3 proteinase inhibitors.

Therefore, the present invention encompasses an isolated polynucleotide encoding a 3' sequence of the GBV-B genome. The polynucleotide may include the sequence identified as SEQ ID NO:1. It is contemplated that the polynucleotide may be a DNA molecule or it can RNA molecule. It is further contemplated that expression constructs may contain a polynucleotide that has a stretch of contiguous nucleotides from SEQ ID NO:1 and/or SEQ ID NO:2, for example, lengths of 50, 100, 150, 250, 500, 1000, 5000, as well as the entire length of SEQ ID NO:1 or 2, are considered appropriate. Such polynucleotides may also be contained in other constructs of the invention or be used in the methods of the invention. Polynucleotides employing sequences from SEQ ID NO:1 may alternatively contain sequences from SEQ ID NO:2 in the constructs and methods of the present invention.

The invention is also understood as covering a viral expression construct that includes a polynucleotide encoding a 3' sequence of the GBV-B genome. This expression construct is further understood to contain the sequence identified as SEQ ID NO:1. The present invention contemplates the expression construct as a plasmid or as a virus. Furthermore, the expression construct can express GBV-B sequences; alternatively it may express sequences from a chimeric GBV-B/HCV virus.

The identification and isolation of a 3' sequence of GBV-B additionally provides a method of producing a virus, particularly a full-length virus, by introducing into a host cell a viral expression construct containing a polynucleotide encoding a 3' sequence of GBV-B and by culturing the host cell under conditions permitting production of a virus from the construct. This method can be practiced using a prokaryotic cell as a host cell, or by using a eukaryotic cell as a host cell. Furthermore, the eukaryotic cell can be located within an animal.

A method of producing virus according to the claimed invention can also be employed using a polynucleotide that contains synthetic RNA and/or synthetic DNA. Moreover, a step can be added to the method by also isolating any virus produced from the host cell. The virus can then be purified to homogeneity.

In further embodiments, the present invention encompasses an oligonucleotide between about 10 and about 259 consecutive bases of SEQ ID NO:1. This oligonucleotide is contemplated to be about 15 bases in length, about 20 bases in length, about 25 bases in length, about 30 bases in length, about 35 bases in length, about 50 bases in length, about 100 bases in length, about 150 bases in length, about 200 bases in length, or about 259 bases in length.

Additional examples of the claimed invention include a method for identifying a compound active against a viral infection by providing a virus expressed from a viral construct containing a 3' sequence of a GBV-B virus, by contacting the virus with a candidate substance; and by comparing the infectious ability of the virus in the presence of the candidate substance with the infectious ability of the virus in a similar system in the absence of the candidate substance. It is contemplated that the invention can be practiced using GBV-B virus or a GBV-B/HCV chimera.

The present invention can also be understood to provide a compound active against a viral infection identified by providing a virus expressed from a viral construct containing a 3' sequence of a GBV-B virus; contacting the virus with a candidate substance; and comparing the infectious ability of the virus in the presence of the candidate substance with the infectious ability of the virus in a similar system in the absence of the candidate substance. In some embodiments an active compound is identified using a GBV-B virus, while in other embodiments an active compound is identified using a GBV-B/HCV chimera.

As used herein the specification, "a" or "an" may mean one or more. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

A. GVB-B Virus

Figure 1:
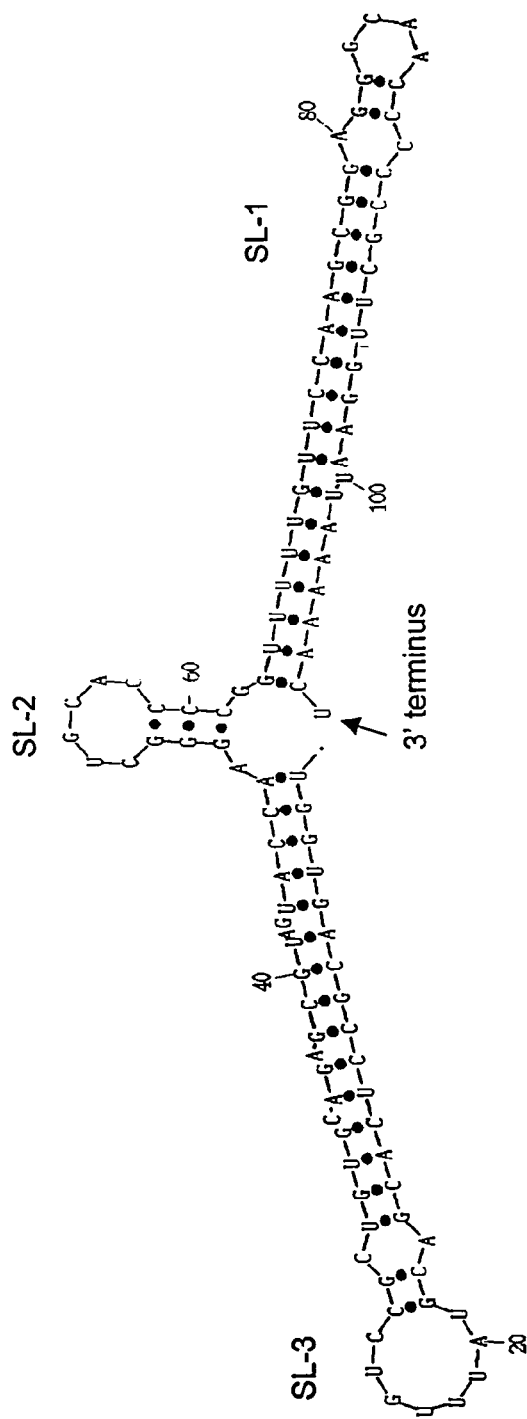
FIG. 1. Predicted secondary RNA structure at the 3' end of the novel 3' GBV-B sequence. The structure shown is that predicted for the 3' terminal 108 nucleotides of the GBV-B genomic RNA by the MFOLD 3.0 computer program of Zucker and Turner, and has an initial free energy of −48 kcal/mole. The predicted structure contains 3 stem-loops, numbered from the 3' end of the genome and labeled SL-1, SL-2, and SL-3. The structure of SL-1 is highly probable, given its terminal position within the genome. Alternative foldings of SL-2 and SL-3 are possible.

The GBV-B genome structure is very similar to hepatitis C and these viruses share approximately 25% nucleotide identity (Simons et al., 1995; Muerhoff et al., 1995). As indicated above, this makes GBV-B more closely related to HCV than any other known virus. GBV-B genomic RNA is about 9.5 kb in length (Muerhoff et al., 1995) with a structured 5' noncoding region that contains an IRES that shares many structural features with the HCV IRES (Honda et al., 1996; Rijnbrand et al., 1999). As in HCV, this IRES drives the cap-independent translation of a long open reading frame. The polyprotein expressed from this reading frame appears to be organized identically to that of HCV, and processed to generate proteins with functions similar to those of HCV (Muerhoff et al., 1995). In fact, the major serine proteinases of these viruses (NS3) have been shown to have similar cleavage specificities (Scarselli et al., 1997). Finally, like HCV and distinct from the pestiviruses, the genomic RNA of GBV-B has a poly(U) tract located near its 3' terminus (Simons et al., 1995; Muerhoff et al., 1995). In addition, unreported sequences located at the extreme 3' end of the genome have been identified. This work indicates that the GBV-B RNA, like that of HCV (HCV (Tanaka et al., 1995; Kolykhalov et al., 1996), terminates in a lengthy run of heterogeneous bases (310 nts in GBV-B) possessing a readily apparent secondary structure

B. NUCLEIC ACIDS

The present invention provides a nucleic acid sequence encoding a 3' sequence of the GBV-B genome (SEQ ID NO:1).

It should be clear that the present invention is not limited to the specific nucleic acids disclosed herein. As discussed below, a "3' sequence of the GBV-B genome" may contain a variety of different bases and yet still be functionally indistinguishable from the sequences disclosed herein. Such functionally indistinguishable sequences are likely to maintain the basic structure depicted in FIGS. 1 and 2, which may be used to guide the prediction of viable nucleotide substitutions.

1. Polynucleotides Encoding the 3' Sequence of the GBV-V Genome

A 3' sequence of the GBV-B genome disclosed in SEQ ID NO:1 is one aspect of the present invention. Nucleic acids according to the present invention may encode the 3' sequence of the GBV-B genome set forth in SEQ ID NO:1, the entire GBV-B genome, or any other fragment of a 3' sequence of the GBV-B genome set forth herein. The nucleic acid may be derived from genomic RNA as cDNA, i.e., cloned directly from the genome of GBV-B. cDNA may also be assembled from synthetic oligonucleotide segments.

It also is contemplated that a 3' sequence of the GBV-B genome may be represented by natural variants that have slightly different nucleic acid sequences but, nonetheless, maintain the same general structure (see FIGS. 1 and 2) and perform the same function in RNA replication.

As used in this application, the term "a nucleic acid encoding a 3' sequence of the GBV-B genome" refers to a nucleic acid molecule that may be isolated free of total viral nucleic acid. In preferred embodiments, the invention concerns nucleic acid sequences essentially as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12. The term "as set forth in SEQ ID NO:1" means that the nucleic acid sequence substantially corresponds to a portion of SEQ ID NO:1. It is contemplated that the techniques and methods described in this disclosure may apply to any of the sequences contained herein, including SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ED NO:12.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 will be sequences that are "as set forth in SEQ ID NO:1." Sequences that are essentially the same as those set forth in SEQ ID NO:1 may also be functionally defined as sequences that are capable of hybridizing to a nucleic acid segment containing the complement of SEQ ID NO:1 under standard conditions.

The nucleic acid segments and polynucleotides of the present invention include those encoding biologically functional equivalent 3' sequences of the GBV-B genome. Changes designed by man may be introduced through the application of site-directed mutagenesis techniques or may be introduced randomly and screened later for the desired function, as described below.

3' sequence of the GBV-B genome sequences also are provided. Each of the foregoing is included within all aspects of the following description. The present invention concerns cDNA segments reverse transcribed from GBV-B genomic RNA (referred to as "DNA"). As used herein, the term "polynucleotide" refers to an RNA or DNA molecule that may be isolated free of other RNA or DNA of a particular species.

"Isolated substantially away from other coding sequences" means that the 3' sequence of the GBV-B genome forms the significant part of the RNA or DNA segment and that the segment does not contain large portions of naturally-occurring coding RNA or DNA, such as large fragments or other functional genes or cDNA noncoding regions. Of course, this refers to the polynucleotide as originally isolated, and does not exclude genes or coding regions later added to the it by the hand of man.

In certain other embodiments, the invention concerns isolated DNA segments (cDNA segments reverse transcribed from GVB-B genomic RNA) and recombinant vectors that include within their sequence a nucleic acid sequence essentially as set forth in SEQ ID NO:1. The term "essentially as set forth in SEQ ID NO:1" is used in the same sense as described above.

It also will be understood that nucleic acid sequences may include additional residues, such as additional 5' or 3' sequences, and still be essentially as set forth in one of the sequences disclosed herein, so long as the sequence meets the criteria set forth above, including the maintenance of biological activity. The addition of terminal sequences particularly applies to nucleic acid sequences that may, for example, include additional various non-coding sequences flanking either of the 5' or 3' portions of the coding region, which are known to occur within viral genomes.

Sequences that are essentially the same as those set forth in SEQ ID NO:1 also may be functionally defined as sequences that are capable of hybridizing to a nucleic acid segment containing the complement of SEQ ID NO:1 under relatively stringent conditions. Suitable relatively stringent hybridization conditions will be well known to those of skill in the art.

The nucleic acid segments of the present invention, regardless of the length of the coding sequence itself, may be combined with other RNA or DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a short contiguous stretch identical to or complementary to SEQ ID NO:1, such as about 15-24 or about 25-34 nucleotides and that are up to about 259 nucleotides being preferred in certain cases. Other stretches of contiguous sequence that may be identical or complementary to any of the sequences disclosed herein, including the SEQ ID NOS. include the following ranges of nucleotides: 50-9,399, 100-9,000, 150-8,000, 200-7,000, 250-6,000, 300-5,000, 350-4,000, 400-3,000, 450-2,000, 500-1000. RNA and DNA segments with total lengths of about 1,000, about 500, about 200, about 100 and about 50 base pairs in length (including all intermediate lengths) are also contemplated to be useful.

In a non-limiting example, one or more nucleic acid constructs may be prepared that include a contiguous stretch of nucleotides identical to or complementary to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12. Such a stretch of nucleotides, or a nucleic acid construct, may be about, or at least about, 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39 about 40, about 45, about 50, about 55, about 60, about 65, about 70, about 75, about 80, about 85, about 90, about 95, about 100, about 105, about 110, about 515, about 120, about 125, about 130, about 135, about 140, about 145, about 150, about 155, about 160, about 165, about 970, about 175, about 180, about 185, about 190, about 195, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 618, about 650, about 700, about 750, about 1,000, about 2,000, about 3,000, about 4,000, about 5,000, about 6,000, about 7,000, about 8,000, about 9,000, about 9,100, about 9,200, about 9,300, about 9,399, about 9,400, about 9,500, about 9,600, about 9,700, about 9,800, about 9,900, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art.

It will be readily understood that "intermediate lengths," in these contexts means any length between the quoted ranges, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, etc.; 100, 101, 102, 103, etc.; 150, 151, 152, 153, etc.; including all integers through the 200-500; 500-1,000; 1,000-2,000; ranges, up to and including sequences of about 1,001, 1,250, 1,500, and the like.

The various probes and primers designed around the disclosed nucleotide sequences of the present invention may be of any length. By assigning numeric values to a sequence, for example, the first residue is 1, the second residue is 2, etc., an algorithm defining all primers can be proposed:

$$n \text{ to } n+y$$

where n is an integer from 1 to the last number of the sequence and y is the length of the primer minus one, where n+y does not exceed the last number of the sequence. Thus, for a 20-mer, the probes correspond to bases 1 to 20, 2 to 21, 3 to 22 . . . and so on. For a 30-mer, the probes correspond to bases 1 to 30, 2 to 31, 3 to 32 . . . and so on. For a 35-mer, the probes correspond to bases 1 to 35, 2 to 36, 3 to 37 . . . and so on.

2. Oligonucleotide Probes and Primers

Naturally, the present invention also encompasses RNA and DNA segments that are complementary, or essentially complementary, to the sequence set forth in SEQ ID NO:1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO. 1 under relatively stringent conditions such as those described herein. Such sequences may encode the entire 3' sequence of the GBV-B genome or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225 or more base pairs will be used, although others are contemplated. Longer polynucleotides encoding 250, 500, 1000, 1212, 1500, 2000, 2500, 3000 or 3431 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary but are mismatched at one or more positions. Conditions may be rendered less stringent by increasing salt concentration and decreasing temperature.

For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

One method of using probes and primers of the present invention is in the search for other viral sequences related to GBV-B or, more particularly, homologs of the GBV-B sequence. By varying the stringency of hybridization, and the region of the probe, different degrees of homology may be discovered.

Another way of exploiting probes and primers of the present invention is in site-directed, or site-specific, mutagenesis. The technique provides a ready ability to prepare and test sequence variants, incorporating one or more of the foregoing considerations, by introducing one or more nucleotide sequence changes into complementary DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement. There are newer and simpler site-directed mutagenesis techniques that can also be employed for this purpose. These include procedures marketed in kit form that are readily available to one of ordinary skill in the art.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

3. Antisense Constructs

In certain embodiments of the invention, the use of antisense constructs of the 3' sequence of the GBV-B genome is contemplated.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs could be used to block early steps in the replication of GBV-B and related viruses, by annealing to 3' terminal sequences and blocking their role in negative-strand initiation.

As stated above, "complementary" or "antisense" means polynucleotide sequences that are substantially complementary over their entire length and have very few base mismatches. For example, sequences of 15 bases in length may be termed complementary when they have complementary nucleotides at 13 or 14 positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

4. Amplification and PCR™

The present invention utilizes amplification techniques in a number of its embodiments. Nucleic acids used as a template for amplification are isolated from cells contained in the biological sample, according to standard methodologies (Sambrook et al., 1989). The nucleic acid may be genomic DNA or RNA or fractionated or whole cell RNA. Where RNA is used, it may be desired to convert the RNA to a complementary DNA using reverse transcriptase (RT). In one embodiment, the RNA is genomic RNA and is used directly as the template for amplification. In others, genomic RNA is first converted to a complementary DNA sequence (cDNA) and this product is amplified according to protocols described below.

Pairs of primers that selectively hybridize to nucleic acids corresponding to GBV-B sequences are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals.

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two or more primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. U.S. Pat. No. 4,883,750 describes a method similar to LCR for binding probe pairs to a target sequence.

Qbeta Replicase, described in PCT Application No. PCT/US87/00880, incorporated herein by reference, also may be used as still another amplification method in the present invention.

An isothermal amplification method, in which restriction endonucleases and ligases are used to achieve the amplification of target molecules that contain nucleotide 5'-[alpha-thio]-triphosphates in one strand of a restriction site also may be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences also can be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter/primer sequence to a target ssDNA followed by transcription of many RNA copies of the sequence. This scheme is not cyclic, i.e., new templates are not produced from the resultant RNA transcripts. Other amplification methods include "RACE" and "one-sided PCR" (Frohman, 1990 incorporated by reference).

Methods based on ligation of two (or more) oligonucleotides in the presence of nucleic acid having the sequence of the resulting "di-oligonucleotide", thereby amplifying the di-oligonucleotide, also may be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography that may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose or nylon, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5. Expression Constructs

In some embodiments of the present invention, an expression construct that encodes a 3' sequence of GBV-B is utilized. The term "expression construct" is meant to include any type of genetic construct containing a nucleic acid coding for a gene product in which part or all of the nucleic acid encoding sequence is capable of being transcribed. The transcript may be translated into a protein, but it need not be. Expression includes both transcription of a gene and translation of mRNA into a gene product. Expression may also include only transcription of the nucleic acid encoding a gene of interest.

In some constructs, the nucleic acid encoding a gene product is under transcriptional control of promoter and/or enhancer. The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies have shown that promoters are composed of discrete functional modules, each consisting of approximately 7-20 bp of nucleic acids, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of nucleic acids with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

6. Host Cells and Permissive Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of the present invention, "host cell" refers to a prokaryotic or eukaryotic cell, and it includes any transformable organisms that is capable of replicating a vector or virus and/or expressing viral proteins. A host cell can, and has been, used as a recipient for vectors, including viral vectors. A host cell may be "transfected" or "transformed," which refers to a process by which exogenous nucleic acid is transferred or introduced into the host cell. A transformed cell includes the primary subject cell and its progeny. A "permissive cell" refers to a cell that supports the replication of a given virus and consequently undergoes cell lysis. In the context of the present invention, such a virus would include HCV, GBV-B, or other hepatitis viruses. In a "nonpermissive cell," productive infection does not result, but the cell may become stably transformed. In some embodiments, methods employ permissive cells that are a cell line derived from liver cells (liver cell line).

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector or virus or virus particle may be used in conjunction with either a eukaryotic or prokaryotic host cell, particularly one that is permissive for replication or expression of the vector. It is contemplated that the present invention includes vectors composed of viral sequences, viruses, and viral particles in the methods of the present invention, and that they may be used interchangeably in these methods, depending on their utility.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

7. Pharmaceutical Compositions

The present invention encompasses the use of a 3' sequence of GVB-B in the production of or use as a vaccine to combat HCV infection. Compositions of the present invention comprise an effective amount of GVB-B clone as a therapeutic dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains GVB-B nucleic acid sequences as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A GBV-B clone of the present invention can be formulated into a composition in a neutral or salt form. Pharmaceutically acceptable salts include the acid addition salts (formed with the free amino groups of the protein) and are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like also can be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

C. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Elucidation of a 3' Sequence of the GBV-B Genome

The inventors elucidated the previously unrecognized 3' terminal sequence of GBV-B (SEQ ID NO 1). This sequence was reproducibly recovered from tamarin serum containing GBV-B RNA, in RT-PCR nucleic acid amplification procedures using several different primer sets, and as a fusion with previously reported 5' GBV-B sequences.

There is information in the published literature reporting the putative sequences of the 5' and 3' termini of the GBV-B genome. The nucleic acid sequences of these termini were reportedly determined by ligating the ends of the viral RNA together, amplifying the sequence in the region of the resulting junction by reverse-transcription polymerase chain reaction (RT-PCR), and sequencing of the cDNA amplification product across the junction. However, the inventors believed these results required confirmation. Of particular concern was the fact that the 3' terminus appeared to be shorter than the equivalent region of other viruses in the family Flaviviridae (especially within the genus *Hepacivirus*) and that the reported 3' sequence lacked a defined RNA hairpin structure such as those present in these related viruses. Additional novel sequences at the 3' end of the GBV-B genome were investigated using a serum sample collected from a tamarin that was experimentally infected with virus. Amplification was used to determine the sequence of the 3' end.

First, serum (50 µL) known to contain GBV-B RNA by RT-PCR assay was extracted with Trizol, and the RNA was washed and dried. A synthetic oligonucleotide was then ligated to the 3' end of the viral RNA. The oligonucleotide, AATTCGGCCCTGCAGGCCACAACAGTC (SEQ ID NO:17), which was phosphorylated at the 5' end and chemically blocked at the 3' end, was ligated to the RNA essentially using the method described by Kolykhalov et al. (Behrens et al., 1996). The RNA was initially dissolved in DMSO and the following additions were made: Tris-Cl, pH 7.5 (10 mM), MgCl$_2$ (10 mM), DTT (5 mM), hexamine cobalt chloride (1 mM), 10 pmol oligo and 8 U T4 ligase. The final concentration of DMSO was 30% in a final volume of 10 μL. The ligation reaction was incubated for 4 or 20 hours at 19° C. 1 μL of the ligation reaction was wed directly to make cDNA, using a primer complementary to the ligated oligonucleotide and the Superscript 2 system, in a final volume of 15 μL. 1 μL of cDNA was amplified using the Advantage cDNA system (Clontech) and two additional oligonucleotide primers. These primers included one that was complementary to the ligated oligonucleotide (i.e., "negative sense") and a positive-sense primer located near the 3' end of the reported GBV-B sequence. A product approximately 290 bases in length was obtained, and this was gel purified and directly sequenced. Sequencing was done in both directions using the oligonucleotide primers employed for the amplification; 259 bases that had not been previously reported were identified as fused to the sequence that had been previously described as the 3' terminus of the viral genome.

To ensure that this novel 3' sequence from viral RNA could be reproducibly amplified, an additional 10 μL of infected tamarin serum was extracted using Trizol. cDNA was prepared by reverse transcription using an oligonucleotide primer complementary to the penultimate 3' 25 bases of the novel sequence. Amplification was then done by PCR using the primer previously utilized for cDNA synthesis and a positive-sense primer mapping within the previously published GBV-B sequence. In the initial experiments, although a product was readily detected, DNA sequencing showed that this product was missing all of the sequence distal to the poly-U tract. Carrying out the cDNA synthesis in the presence of DMSO circumvented this problem. A cDNA product of approximately 290 bases was obtained. This was sequenced and shown to consist of the 5' primer, 20 bases of the published GBV-B sequence, and 259 bases of the novel sequence obtained in the preceding experiments and containing the sequence of the 3' primer. The sequence of the 3' end of GBV-B is shown in SEQ ID NO: 1 (FIG. 1). The possible secondary RNA structure for this region is shown in FIG. 2, as predicted by a computer-based RNA folding program. The presence of a predicted hairpin structure at the extreme 3' end of this novel sequence is consistent with its location at the 3' terminus of the viral RNA.

The GBV-B cDNA (synthesis described above) was used as a template for PCR amplification of the 3' 1553 nucleotides (nts) of the GBV-B genome. This PCR amplification product was gel purified and cloned into plasmid DNA using the "Perfectly Blunt Cloning Kit" (Novagene).

Example 2

Construction of an Infectious GBV-B Clone

The elucidation of a 3' sequence of the GBV-B genome will allow those of skill in the art to construct and validate an infectious molecular clone of GBV-B. This will be done using the following procedures.

A full-length cDNA copy of the GBV-B genome containing the newly identified 3' terminal sequences was constructed. RNA transcribed from this cDNA copy of the genome will be infectious when inoculated into the liver of a GBV-B permissive tamarin, giving rise to rescued GBV-B virus particles.

A 1:1000 dilution of GBV-B infectious tamarin serum was obtained. This material was used as a source of viral RNA for the amplification of GBV-B nucleic acid sequences by reverse-transcription polymerase chain reaction. For amplification of previously reported segments of the GBV-B genome, 250 μL of the diluted serum was extracted with Trizol using the manufacturer's instructions. The final RNA pellet was dissolved in 10 μL of a 100 mM DTT buffer containing 5% RNasin. This material was converted into cDNA using Superscript 2 reverse transcriptase and oligonucleotide primers designed to be complementary to the reported GBV-B RNA sequence and to contain unique restriction sites. This cDNA was amplified using the Advantage cDNA kit (Clontech) employing the cDNA primer (negative sensiv as the downstream primer and a similar positive-sense upstream primer, again containing a unique restriction site. The published sequence of GBV-B allowed for the selection of primers in convenient areas of the genome containing unique restriction sites. Using this general strategy, the inventors amplified segments of the reported GBV-B genome representing: (1) nucleotides (nts) 1-1988, using an upstream primer containing a T7 RNA polymerase promoter and a BamH1 site upstream of nt 1, and a downstream primer containing a unique EcoIR1 site (nt 1978); (2) nts 1968-5337, using a downstream primer containing a unique Cla1 site at position 5o27; (3) nts 5317-7837, using a downstream primer containing a Sal1 site at nt 7847; and, (4) nts 7837-9143, using a downstream primer containing an added XhoI site. It was found necessary to use different PCR conditions for each primer set.

The RT-PCR products generated in these reactions were cloned into plasmid DNA after gel purification, using the "Perfectly Blunt Cloning Kit" (Novagene). Ten bacterial colonies from each of the four RT-PCR products were analyzed for insert size by restriction endonuclease digestion using EcoRI, the sites for this enzyme being located on either side of the insert in the resulting plasmids. For three of the RT-PCR amplicons, 9 of 10 colonies contained plasmids with the correct size insert. The EcoR1-Cla1 amplicon generated only ¹⁄₁₀ colonies with a correct size insert. Thus, 30 additional colonies were examined, yielding two more clones with insert of the correct size. For each of these plasmids, simple restriction patterns were obtained using two restriction enzymes. As these appeared to be correct, the plasmid DNAs were subjected to sequencing using an ABI automatic sequencer.

Example 3

Nucleotide Sequence of the Cloned GBV-B cDNA

The 5' region of the cloned sequence revealed a relatively long nontranslated region corresponding to the published sequence of the GBV-B 5'NTR, which includes an IRES. This region was followed by a long open reading frame. Near the 3' end of the genome a poly-U tract was identified; however, this was shorter than the published 3' homopolymeric poly-U region. The sequence from these clones was compared with those in the GenBank database (Accession U22304, "Hepatitis GB virus B polypeptide complete genome"). Twenty-two nucleotide differences were identified, of which 14 gave rise to amino acid changes (Table 1). In order to determine whether these changes were genuine or RT-PCR artifacts, which could have been introduced due to the very small amount of material from which these sequences were amplified, segments of the genome containing these changes were reamplified using a serum sample from an independently infected tamarin. Of the 14 changes noted in the original cDNA clones, 12 were not present in these newly amplified sequences and thus were probably RT-PCR artifacts (Table 2.). A particularly interesting difference from the published GenBank sequence, however, which was present in both the original clones as well as a repeat amplification, was a two-nucleotide substitution that obliterated the Sal1 site present in the published sequence.

TABLE 1

Differences in the amino acid sequences of GBV-B cDNA clones and the GBV-B sequence reported by Simons et al. (1995).

| GBV-B Protein | AMINO ACID Δ FROM ABBOTT SEQUENCE | RT-PCR Products from Tamarin 12024 (PCR Reaction #) |
|---|---|---|
| Core | $G_{99} \rightarrow S$ | G (38.1a) |
| E1 | $V_{395} \rightarrow I$ | V (40.2a) |
| E2 | $D_{703} \rightarrow N$ | D (42.3a) |
| E2 | $P_{706} \rightarrow Q$ | H (42.3a) |
| E2 | $A_{728} \rightarrow V$ | A (42.3a) |
| NS2 | $L_{791} \rightarrow F$ | F (42.3a) |
| NS2 | $T_{804} \rightarrow A$ | A (42.3a) |
| NS5A | $L_{1990} \rightarrow M$ | L (46.5a) |
| NS5A | $I_{2082} \rightarrow T$ | I (46.5a) |
| NS5A | $S_{2174} \rightarrow P$ | (not done) |
| NS5A | $G_{2228} \rightarrow E$ | E (48.6a) |
| NS5A | $T_{2233} \rightarrow S$ | T (48.6a) |
| NS5A | $A_{2236} \rightarrow V$ | A (48.6a) |
| NS5B | $V_{2833} \rightarrow I$ | V (50.7a) |

Example 4

Construction of a Full-Length GBV-B cDNA Clone

The four GBV-B cDNA inserts described above were cloned into Bluescript ks+ using unique restriction sites. Since the unique Sal1 site that was reported to be present in the published GBV-B sequence (nt position 7847) was absent in these cDNA clones, this restriction site was created by engineering two silent nucleotide changes using the "Quick Change" mutagenesis system (Stratagene). Although the most 5' clones (nucleotides 1-7847) could be readily constructed, attempts to add the remaining 3' clones were unsuccessful due to rearrangements and deletions. This problem was overcome by use of pACNR1180, a plasmid that had been used to construct an infectious clone of yellow fever virus. Finally, the most 3' 771 nucleotides of GBV-B were excised from the plasmid containing the novel, previously unreported 3' sequence, and inserted into the truncated assembled GBV-B cDNA construct to complete the 3' end. The 3' terminus of this full-length cDNA was then subjected to DNA sequencing to confirm its integrity. Extensive restriction digests indicated that this construct had the characteristics of a full-length c DNA copy of GBV-B virus. Because there is not yet an understanding of which cultured cells (if any) might be permissive for GBV-B replication, the infectivity of the synthetic GBV-B RNA will be assessed by injecting the RNA directly into the liver of a susceptible tamarin.

Alternatively, an infectious full-length clone can be produced by the following protocol. A plasmid will be made containing a cassette including the 5' and 3' ends of the virus flanked by appropriate restriction sites. These constructs have been shown to efficiently translate reporter genes, with transcription taking place via a T7 promoter placed immediately upstream of the 5'NTR (e.g., see Rijnbrand et al., 1999). The major portion of the GBV-B genome would then be amplified by long range RT-PCR. This method is now well established for hepatitis C virus and other flaviviruses (Teller et al., 1996), and it has been used successfully also to amplify rhinovirus RNA. Briefly this technique uses "Superscript" reverse transcriptase to synthesize cDNA and a mixture of "KlenTaq 1", and "DeepVent" polymerases to amplify this cDNA. Primers that can be used will contain restriction sites to allow cloning of the RT-PCR products into the cassette vector. After being transformed into suitable competent bacteria, extensive restriction analysis will enable us to determine which clones contain inserts that are of full length and which have a high probability of being correct. Apparent full-length clones will be analyzed further by coupled transcription-translation using the Promega "TnT" system, with the addition of microsomal membranes to allow the cleavage of the structural proteins by cellular signalase enzymes. Clones which appear correct by restriction analysis and which produce GBV-B proteins, in particular the protein coded for by the extreme 3' end of the genome, NS5B, will be selected, and RNA will be transcribed from these clones using the Ambion MegaScript system. "Correct" looking clones (>10) can be injected directly into a tamarin liver at several sites. A successful infection will be determined as described below. If a positive signal is detected the entire genome will be amplified and sequenced to determine which plasmid the virus originated from.

Example 5

Rescue of Infectious GVB-B

Infectious GBV-B will be rescued from synthetic genome-length RNA following its injection into the liver of tamarins (*Saquinus* sp.). In past studies, HAV from synthetic RNA in owl monkeys has been recovered (*Aotus trivirgatus*) (Shaffer et al., 1995), and more recently, the recovery of virus from a chimpanzee injected intrahepatically with RNA transcribed from a full-length genotype 1b HCV cDNA clone was reported (Beard et al., 1999).

RNA will be prepared for these experiments using the T7 MegaScript kit (Ambion) and a total of 10 μg of plasmid DNA as template. An aliquot of the reaction products will be utilized to ensure the integrity of the RNA by electrophoresis in agarose-formaldehyde gels. The remainder of the transcription reaction mix will be frozen at −80 C.° until its injection, without further purification, into the liver of a tamarin. Because of the small size of the tamarin, the RNA will be injected under direct visualization following a limited incision and exposure of the liver. Under similar conditions, in other primate species, RT-PCR-detectable viral RNA or cDNA has not been detected in serum samples collected within days of this procedure in the absence of viral replication (Kolykhalov et al., 1997; Yanagi et al., 1998; Beard et al., 1999). Thus, the appearance of RNA in serum collected subsequently from these tamarins will be strong evidence for the replication competence of the synthetic RNA. Serum will be collected weekly for six weeks, then every other week for an additional 6 weeks from inoculated animals. In addition to RT-PCR for detection of viral RNA (see FIG. 2B), alanine aminotransferase (ALT) levels will be measured as an indicator of liver injury and to assess liver histology in punch biopsies taken at the time of ALT elevation. Maximum viremia and an acute phase ALT response is expected to occur around 14-28 days post-inoculation of infectious RNA (Simons et al., 1995; Schlauder et al., 1995; Karayiannis et al., 1989). Transfections will be considered to have failed to give rise to infectious virus if RNA is not detected in the serum within 12 weeks of inoculation. Successfully infected animals will Example 6

Construction of GBV-B/HCV Chimeras

The GBV-B genome can be used as the acceptor molecule in the construction of chimeric viral RNAs containing sequences of both HCV and GBV-B. Such constructs will allow one to investigate the mechanisms for the different biological properties of these viruses and to discover and investigate potential inhibitors of specific HCV activities (e.g., proteinase) required for HCV replication. Different classes of chimeric viruses are contemplated. These include: (a) replacement of the GBV-B IRES with that of HCV; and (b) replacement of the NS3 major serine proteinase and helicase, and (c) the replacement of the NS5B RNA-dependent RNA polymerase with the homologous proteins of HCV.

The chimeric constructs described in the following sections will be made by PCR mutagenesis, using high fidelity polymerases and oligonucleotide primers designed to include the specific fusions of GBV-B and HCV sequences (Landt et al., 1990). First round PCR reactions will create the desired fusion, and generate a new "primer" to be used in a second PCR reaction spanning the region to a convenient unique restriction site. PCR cycles will be kept to the minimum number necessary for successful amplification, and all segments of viral sequence that are amplified by PCR will be subjected to DNA sequencing to exclude the presence of unwanted PCR-introduced errors. Sequencing will be accomplished at UTMB's core Recombinant DNA Laboratory. Amplified segments will be kept to the minimum by the exchange of cloned cDNA segments spanning convenient restriction sites in subgenomic clones, and where necessary PCR artifacts can be corrected by site-directed mutagenesis (QuickChange mutagenesis kit, Stratagene).

A number of viable positive-strand RNA virus chimeras have been constructed previously in which IRES elements have been swapped between different viruses. Most of these chimeras have involved the exchange of IRES elements between picornaviruses. Others have been successful in constructing viable poliovirus chimeras containing the HCV IRES in place of the native poliovirus IRES (Zhao et al., 1999; Lu and Wimmer, 1996). A similar rhinovirus 14 chimera containing the HCV IRES has been constructed, although its replication phenotype is not as robust as the poliovirus chimera described by Lu and Wimmer (Lu and Wimmer, 1996). More importantly, Frolov et al. (Frolov et al., 1998) recently reported chimeric flaviviruses in which the HCV IRES was inserted into the genetic background of a pestivirus, bovine viral diarrhea virus (BVDV) in lieu of the homologous BVDV sequence. Although these viable chimeric polioviruses and pestiviruses replicate in cell cultures, they are poor surrogates for HCV in animal models as neither virus is hepatotropic or causes liver disease. Importantly, Frolov et al. (Frolov et al., 1998) demonstrated quite convincingly that the requirement for cis-acting replication signals at the 5' terminus of the pestivirus genome was limited to a short tetranucleotide sequence. This requirement presumably reflects the need for the complement of this sequence at the 3' end of the negative strand during initiation of positive-strand RNA synthesis. The work of Frolov et al. shows that the IRES of BVDV does not contain necessary replication signals, or that if these are present within the BVDV IRES they can be complemented with similar signals in either the HCV or encephalomyocarditis virus (EMCV, a picornavirus) IRES sequence. Since GBV-B and HCV are more closely related to each other than BVDV and HCV, these studies provide strong support for the viability of chimeras containing the HCV IRES in the background of GBV-B.

Construction of a viable IRES chimera will be enhanced by studies that have documented the sequence requirements and secondary structures of the IRES elements of both HCV and GBV-B (see Lemon and Honda, 1997; Honda et al., 1996; Rijnbrand et al., 1999). To a considerable extent, the work of Frolov et al. (Frolov et al., 1998) was guided by studies of the HCV IRES structure. More recently, these studies have been extended to include a detailed mutational analysis of the GBV-B IRES. The results of these experiments indicate that the functional IRES of GBV-B extends from the 5' end of structural domain II (nt 62) to the initiator AUG codon (nt 446). This segment of the full-length GBV-B clone will be replaced with HCV sequence extending from 5' end of the analogous domain II within the HCV IRES (nt 42) to the initiator codon at the 5' end of the HCV open reading frame (nt 341) to construct the candidate chimera, "GB/C:IRES". The source of HCV cDNA for these studies will be the infectious HCV clone, pCV-H77C, which contains the sequence of the genotype 1a Hutchinson strain virus (Yanagi et al., 1998), whose infectivity in a chimpanzee following intrahepatic inoculation with synthetic RNA transcribed from pCV-H77C has been confirmed.

This GB/C:IRES construct will retain two upstream hairpins within the GBV-B sequence (stem-loops Ia and Ib), and it is thus analogous to the viable "BVDV+HCVdelB2B3H1" chimera of Frolov et al (Frolov et al., 1998). A second chimera can be constructed in which the entire HCV 5' nontranslated RNA will be inserted in lieu of nts 62-446 of the GBV-B genome ("GB/C:5'NTR"). This construct will add to the inserted HCV sequence the most 5' stem-loop from HCV (stem-loop I). A similar insertion was shown to substantially increase the replication capacity of BVDV+ HCVdelB2B3H1 by Frolov et al. (Frolov et al., 1998), providing a replication phenotype similar to wild-type BVDV in cell culture.

It is important to point out that there is strong evidence from multiple lines of investigation indicating that it will not be necessary to include coding sequence in these IRES chimeras. This is the case even though Reynolds et al. (Reynolds et al., 1995) have argued that the HCV IRES extends past the initiator codon, and into the core-coding region of that virus. Although Lu and Wimmer (Lu and Wimmer, 1996) found it necessary to include HCV core sequence to obtain a viable chimeric poliovirus, the BVDV chimeras reported by Frolov et al. (Frolov et al., 1998) did not contain any HCV coding sequence. This discrepancy may be explained by the observation that the only downstream requirement for full activity of both the GBV-B and HCV IRES elements is the presence of an unstructured RNA segment (Honda et al., 1996; Rijnbrand et al., 1999). Presumably, this facilitates interaction of the viral RNA with the 40S ribosome subunit in the early steps of cap-independent translation (Honda et al., 1996). The 5' GBV-B coding sequence fulfills this criterion (Rijnbrand et al., 1999).

Example 7

In Vitro Characterization of the Translational Activity of IRES Chimeras

The fidelity of the genome-length chimeric constructs will be confirmed by sequencing any DNA segments that have been subjected to PCR during the construction process, as well as confirming sequence at the junction sites. In addition, the translational activity of synthetic RNA derived from these constructs will be assessed and compared to the translational activity of the wild-type GBV-B and HCV RNAs. These studies will be carried out in a cell-free translation assay utilizing rabbit reticulocyte lysates (Rijnbrand et al., 1999). Synthetic RNA will be produced by runoff T7 RNA polymerase transcription using as template ClaI-digested plasmid DNA (BamHI digestion in the case of the genome HCV construct) (T7 Megascript kit, Ambion). $^3$H-UTP will be added to the reaction mix to allow for quantification of the RNA product. Reticulocyte lysates (Promega) will be programmed for translation by the addition of RNA (at least 50% full-length as determined by agarose gel electrophoresis) at 20, 40 and 80 µg/ml, and translation reactions will be supplemented with microsomal membranes (Promega). $^{35}$S-Methionine-labelled translation products will be separated by SDS-PAGE, and the quantity of E1 protein produced from each RNA determined by PhosphorImager analysis (Molecular Dynamics). Comparisons of the activity of the HCV IRES in the background of GBV-B and HCV will take into account differences in the methionine content of the E1 proteins of these viruses. Based on previous studies of both the GBV-B and HCV IRES elements (Honda et al., 1996; Rijnbrand et al., 1999), it is expected that these studies will confirm that the HCV IRES will retain nearly full activity when placed within the GBV-B background.

Example 8

In Vivo Characterization of IRES Chimeras

Synthetic RNAs produced from each of the two chimeric GBV-B/HCV constructs (GB/C:IRES and GB/C:5'NTR) will be tested for their ability to induce infection and cause liver disease in susceptible tamarins. These experiments will be carried out as described in Example 2. GB/C:5'NTR may generate viremia and liver injury more closely resembling that observed with wild-type GBV-B infection (Frolov et al., 1998).

Example 9

Chimeric Flaviviruses Containing the HCV NS3 Serine Proteinase/Helicase within the GBV-B Background Chimeric flaviviruses containing the HCV NS3 serine proteinase/helicase within the GBV-B background are also contemplated within the present invention. The construction of chimeric flaviviruses containing specific heterologous functional polyprotein domains, however, poses a number of special problems. Unlike the situation with the IRES, where the relevant RNA segments appear to have a unique function restricted to cap-independent translation initiation and interact with host cell macromolecules, viral proteins often have multiple functions and may form specific macromolecular complexes with other viral proteins that are essential for virus replication (Lindenbach and Rice, 1999). Furthermore, such chimeric polyproteins must be amenable to efficient processing by the viral proteinases (NS2/NS3 or NS3). This requires knowledge of the proteinase cleavage specificities as well as specific sites of proteolytic cleavage. Although to date there have been no published studies of the processing of the GBV-B polyprotein, the relatively close relationship between GBV-B and HCV, about 30% overall amino acid identity within the polyprotein (Muerhoff et al., 1995), allows good computer predictions of the alignments of these proteins. The crystallographic structures of both the proteinase and helicase domains of the HCV NS3 protein have been solved (Yao et al., 1997). Thus, both linear alignments and models of the 3D structure of the NS3 proteins of these viruses can provide guidelines for designing specific chimeric fusions that are likely to preserve function.

Example 10

NS3 Proteinase-Domain Chimeras

In HCV, NS3 contains the major serine proteinase that is responsible for most cleavage events in the processing of the nonstructural proteins, i.e., those that occur at the NS3/4A, 4A/4B, 4B/5A and 5A/5B junctions. The active proteinase domain of HCV is located within the amino terminal third of the NS3 protein (residues 1-181), which shares 31% amino acid identity with the analogous segment of the GBV-B polyprotein (GBV-B vs HCV-BK) (Muerhoff et al., 1995). Importantly, the active site of this proteinase appears to be particularly well conserved in GBV-B. The GBV-B proteinase maintains the residues that are responsible for catalysis and zinc binding in the HCV enzyme (Muerhoff et al., 1995), and unlike the NS3 proteinases of some other flaviviruses preserves the Phe-154 residue that determines in part the $S_1$ specificity pocket of the enzyme and the preference of the HCV proteinase for substrates with a cysteine residue at the P1 position (Scarselli et al., 1997). Thus, it is not surprising that the relevant proteolytic cleavage sites within the GBV-B polyprotein that are predicted from alignments with the HCV polyprotein all possess a Cys residue at this position. Of greatest significance for the proposed experiments, however, is the work of Scarselli et al. (Scarselli et al., 1997) who demonstrated that the GBV-B NS3 proteinase is able to effectively process the polyprotein of HCV in experiments carried out in vitro. Using synthetic peptide substrates, these investigators demonstrated that the enzymatic activities of the GBV-B proteinase (residues 1-181) had kinetic parameters similar to the HCV proteinase on NS4A/4B and NS4B/4A substrates HCV. They did not possess reagents allowing a determination of whether the HCV proteinase is able to cleave a GBV-B substrate, but their results indicate that these viral proteinases share important functional properties. Therefore, these similarities suggest that the HCV proteinase could function in lieu of the GBV-B proteinase if used to replace this segment of an infectious GBV-B clone. In addition, experiments with sindbis/HCV chimeras have shown that the HCV proteinase can cleave within the framework of a sindbis polyprotein (Filocamo et al., 1997).

In considering the design of these NS3 proteinase chimeras, there are two additional important considerations. First, in HCV, the cleavage between NS2 and NS3 occurs in cis, as the result of a zinc-dependent metalloproteinase that spans the NS2/NS3 junction (Hijikata et al., 1993). As only the NS3 sequences will initially be exchanged, the viability of the resulting chimeras will be dependent upon preservation of the cis-active cleavage across a chimeric NS2/NS3 proteinase domain. The alignment of GBV-B and HCV sequences shows that residues in HCV that have been shown by Grakoui et al., 1993, to be essential for the NS2/NS3 cleavage are conserved in GBV-B (Muerhoff et al., 1995). Additional chimeras that will include the relevant carboxyl-terminal portion of NS2 can also be created.

A second important consideration is that the mature HCV NS3 proteinase functions as a noncovalent assembly of the NS3 proteinase domain and the amino terminal portion of NS4A, a proteinase accessory factor. The details of this association are well known, and have been studied at the crystallographic level (Kim et al., 1996). The N-terminal domain of the folded proteinase contains eight β strands, including one contributed directly by the NS4A peptide backbone. X-ray studies have shown that this array of β strands gives rise to a much more ordered N-terminus. Thus, the presence of the NS4A strand seems likely to contribute to the structure of the substrate-binding pocket. It is not known whether the NS3 proteinase of GBV-B also requires a similar interaction with NS4A of that virus for complete activity, or, if so, whether the NS4A of GBV-B could substitute for NS4A of HCV in forming the fully active NS3 proteinase of HCV. The predicted GBV-B NS4A molecule is 54 amino acid residues in length (Simons, et al., 1995; Muerhoff et al., 1995), just as in HCV. However, the level of amino acid homology between the NS4A molecules is not especially high, and the potential interaction with either NS3 molecule cannot be predicted from this sequence on the basis of available knowledge. To overcome this potential problem, chimeras will be created in which not only the NS3 proteinase domain of GBV-B is replaced, but also the relevant NS4A segment as well, with homologous segments of the HCV polyprotein. The interaction of the HCV NS3 and NS4A domains represents a unique target for antiviral drug design, and it would be beneficial to have this specific interaction present in any virus to be used as a surrogate for HCV in the evaluation of candidate antiviral inhibitors of HCV proteinase in vivo.

The NS3 proteinase chimeras that can be made include "GB/C:NS3$^P$", which will contain the sequence encoding the first 181 amino acid residues of the HCV NS3 molecule in lieu of that encoding the first 181 residues of GBV-B NS3, and "GB/C:NS3$^P$4A", which will include the same NS3 substitution as well as the HCV sequence encoding the amino-terminal segment of NS4A that forms the interaction with NS3. The precise NS4A sequence to be included in the latter chimera will be based on the modeling studies, which may also suggest more effective fusions of the NS3 proteinase domain of HCV with the downstream NS3 helicase domain of GBV-B. The source of HCV cDNA for these experiments will be the infectious HCV clone, pCV-H77C, which contains the sequence of the genotype 1a Hutchinson strain virus (Yanagi et al., 1998).

Example 11

NS3 Helicase Domain Chimeras

In addition to serine proteinase activity located within the amino-third of NS3, the downstream carboxy-terminal two-thirds of the molecule contains an RNA helicase activity. These two functional domains appear to be separated by a flexible spacer, within which the fusion of HCV proteinase or helicase domain sequences with GBV-B sequence will be placed. The exact role of the helicase in the HCV life-cycle is not known, but it is almost certainly required for dsRNA strand-separation during some phase of viral RNA synthesis. The helicase domains of GBV-B and HCV are remarkably well conserved, with some regions within the helicase showing as much as 55% amino acid identity (Muerhoff et al., 1995). The GBV-B helicase is more closely related to the HCV helicase than all other flaviviral NS3 helicases, and it preserves many residues found within the conserved helicase motifs of HCV. Thus the HCV NS3 helicase may be capable of functioning when placed within the polyprotein of GBV-B, and such a chimeric virus may be capable of replication. Residues 182-620 of the GBV-B NS3 molecule will be substituted with the analogous segment of HCV (FIG. 5, "GB/C:NS3$^h$"). A chimera will also be made in which the entire NS3 and amino terminal NS4 protein sequences of GBV-B is replaced with the homologous HCV sequences ("GB/C:NS3-4A"). The latter construct will thus represent a dual proteinase-helicase chimera. As with the proteinase chimeras, the HCV cDNA will be derived from pCV-H77C (Yanagi et al., 1998).

Example 12

In Vitro Characterization of NS3 and NS3-NS4A Chimera

Prior to being evaluated for infectivity in susceptible tamarins, RNAs produced in vitro from these clones will characterized in vitro. This evaluation will be restricted to a documentation of the proper processing of the expressed polyprotein (i.e., NS2/NS3 and NS3 proteinase functions), since there are no relevant assays that can determine whether the helicase or RNA-dependent RNA polymerase activities in these polyproteins are sufficient for virus replication. The proteolytic processing of the polyprotein is important, however, as it may be altered either by inclusion of the heterologous HCV NS3 proteinase in lieu of the natural GBV-B protease, or by a change in the folding of the polyprotein induced by inclusion of HCV sequence anywhere within the polyprotein. These studies will be carried out in cell-free coupled transcription/translation assays ("TnT" system, Promega) supplemented with microsomal membranes. Template DNAs will be digested with SalI, which restricts the cDNA within the NS5B coding region. $^{35}$S-methionine-labelled translation products will be separated by SDS-PAGE, and the mature NS3 protein identified by its apparent molecular mass. The NS3 and NS5B proteins will be identified by immunoblot analysis using rabbit antisera to the GBV-B NS3 and NS5B proteins. Generation of a mature ~68 kDa NS3 protein will provide proof of both the cis-active NS2/NS3 cleavage and the NS3-mediated cleavage of NS3/NS4A. Similarly, identification of a mature, processed NS5B molecule will provide further support for the activity of the NS3 proteinase. Controls for these experiments will be the wild-type GBV-B polyprotein expressed in similar fashion from the full-length GBV-B clone. If necessary to more clearly demonstrate the processing of the nonstructural proteins in these constructs, subclones representing the nonstructural region of the chimeric sequences could be produced.

Example 13

In Vivo Characterization of NS3 and NS3-4A Chimeras
Synthetic RNAs produced from each of the chimeric GBV-B/HCV constructs described in the preceding section will be tested for their ability to induce infection and cause liver disease in susceptible tamarins. These experiments will be carried out using the approach described above.

Example 14

Chimeric Flaviviruses Containing the HCV NS5B RNA Dependent RNA Replicase within the GBV-B Background The HCV NS5B molecule contains an RNA-dependent RNA polymerase that plays a central role in replication of the virus. Although this molecule represents a prime target for drug discovery efforts, it has proven difficult to express NS5B in a form that retains enzymatic activity specific for HCV RNA as a substrate. Thus, relatively little is known of the functional activity of the HCV replicase, including structure-function relationships of NS5B. Despite this, the NS5B proteins of GBV-B and HCV appear to be functionally closely related, as they share as much as 43% amino acid identity (Muerhoff et al., 1995). A more important question may be whether an RNA dependent RNA polymerase can act on foreign substrates. However, published work has shown that in vitro purified HCV polymerase has very little specificity for its template, using hepatitis C or globin message with equal fidelity (Behrens et al., 1996; Al et al., 1998). This finding is very similar to that obtained with picornaviral polymerases, where it has been known for many years that in vitro the enzyme exhibits very little specificity. It has always been considered highly likely that this situation would not pertain in vivo where it was thought that the interaction of viral or cellular factors with the 3' end of the genome would generate template specificity. However, recent reports have shown that the removal of the entire 3' untranslated sequence (leaving, however, the poly(A) region present) from both the poliovirus and rhinovirus genome does not completely abrogate the infectivity of the virus (Todd et al., 1997). Furthermore, virus, which was recovered after the initial transfections, was shown to have recovered much of the infectivity of the original virus (Todd et al., 1997). The mechanism for this recovery of infectivity is at present unknown, but these results suggest that the HCV polymerase may be able to function to replicate infectious GBV-B/HCV NS5B chimeras.

Thus a chimeric genome-length virus can be created in which the NS5B coding sequence of HCV (amino acids 2422-3014, 593 residues) is inserted within the background of GBV-B in lieu of its native RNA-dependent RNA polymerase (amino acids 2274-2864, 591 residues). This chimeric virus would be valuable for animal studies of candidate antiviral inhibitors of HCV RNA synthesis.

This NS5B chimera would be evaluated to determine that there was proper proteolytic processing of the polyprotein. This would be accomplished by expression of the chimeric polyprotein in a coupled translation-transcription reaction, followed by immunoblot analysis for the mature NS5B protein, as described for the NS3 and NS3-4A chimeras in the preceding section. If these results confirm that the GB/C:5B chimeric polyprotein is processed with release of NS5B, experiments in tamarins would progress to determine whether synthetic RNA transcribed from the clone is infectious and capable of causing liver disease in intrahepatically inoculated animals. These experiments would be carried out as described above.

A chimeric molecule can be constructed from an infectious GBV-B clone in which the HCV NS3 proteinase or proteinase/helicase sequence would be placed in frame in lieu of the homologous GBV-B sequence, and this chimeric cDNA would be used to generate infectious GBV-B/HCV chimeric viruses by intrahepatic inoculation of synthetic RNA in tamarins. Published studies indicate that the GBV-B and HCV proteinases have closely related substrate recognition and cleavage properties, likely making such chimeras viable and capable of initiating viral replication in appropriate cell types.

Example 15

Chimeric Viruses Containing HCV Structural Proteins within a GBV-B Genetic Background, and GBV-B Structural Proteins within an HCV Background It is well documented that the structural proteins of one flavivirus may in some cases be substituted for those from another member of the family. Such chimeric viruses have been recovered from viruses as distantly related to each other as dengue virus and tick-borne encephalitis virus (Pletnev et al., 1992). More recently, the prM and E proteins of Japanese encephalitis virus have been used to replace the equivalent proteins in a vaccine strain of yellow fever virus to produce a JE/YF chimera (Chambers et al., 1999). These observations suggest that chimeras in which the structural proteins of HCV have been used to replace the homologous proteins of GBV-B may well be viable and capable of replication. The isolation of a chimeric virus containing HCV structural proteins, but having the growth characteristics of GBV-B virus, could answer many fundamental questions concerning the structure and interaction of these proteins in HCV. They would also be useful in addressing the nature of the immune response to HCV structural proteins in infected primates (Farci et al., 1992). More to the point of this application, the availability of such chimeric viruses would allow studies of candidate HCV vaccines to be carried out in the tamarin model. This would be a major advance, because at present such studies are limited to chimpanzees (Choo et al., 1994).

The basis for the difference in the host ranges of HCV and GBV-B is completely unknown. Among many other possibilities, it is conceivable that the host range is dependent upon the availability of a specific receptor(s). If this were the case, host range might be dependent upon the envelope proteins that must interact with the putative cellular receptor. Thus, a chimeric virus containing the envelope proteins of HCV within the genetic background of GBV-B might be noninfectious in tamarins (but potentially infectious in chimpanzees). Thus, a finding that both structural protein chimeras are noninfectious in the tamarin, may require the construction of complementary chimeras in which the relevant GBV-B structural proteins will be inserted into the background of an infectious HCV clone. If inclusion of the GBV-B envelope proteins within the backbone of HCV confers on the resulting chimera the ability to replicate in tamarins, it will confirm an important role for the structural proteins in defining the different host ranges of these viruses. More importantly, the resulting virus would be an exceptionally valuable resource for future studies as it would contain all of the nonstructural replication elements, as well as the 5' and 3' nontranslated regions, of HCV. Such a virus would allow the tamarin model to be used to address many unresolved issues in HCV biology and pathogenesis.

Example 16

Construction and Evaluation of Structural Protein Chimeras

In designing structural protein chimeras, it is important to note that the two envelope proteins of HCV, E1 and E2, form noncovalent heterodimeric complexes that are likely to be important in the assembly of infectious virus particles. This is not known to be the case with the envelope proteins of GBV-B, but it is likely given similarities in the sizes and hydropathy profiles of these proteins (Simons et al., 1995; Muerhoff et al., 1995). Accordingly, the E1 and E2 proteins will be replaced as a unit, and chimeras containing only one of these proteins from the heterologous virus will generally not be produced. First, a chimera will be created where the E1 and E2 regions of GBV-B virus are replaced with those of HCV, "GB/C:E1-2". The source of HCV cDNA for these constructions will be pCV-H77C (Yanagi et al., 1998). A chimera will also be made in which the core protein, in addition to the envelope proteins, is replaced with the homologous proteins of HCV ("GB/C:Co-E2"). Additional chimeras will be made to determine whether tamarins can be infected with chimeras containing the GBV-B structural proteins within the genetic background of HCV. These will include "C/GB:E1-2" and "C/GB:Co-E2". The backbone for these chimeras will be pCV-H77C, the infectious genotype 1a cDNA clone developed in the Purcell laboratory at NIAID (Yanagi et al., 1998).

The specific amino acid sequences of GBV-B to be replaced with the homologous segments of HCV have been determined by alignments of the GBV-B and HCV sequences, coupled with the location of signalase cleavage sites predicted to be present within the amino terminal third of the GBV-B polyprotein using the computer algorithm of Von Heijne. These predicted signalase cleavages lie between residues 156/157 (core/E1), aa 348-349 (E1/E2) and 732/733 (E2/NS2) in the GBV-B sequence. Thus, the chimera GB/C:E1-2 will contain sequence encoding HCV aa 192-809 in lieu of that encoding aa 157-732 in GBV-B, while the insertion in the GB/C:Co-E2 chimera will extend from the initiator AUG codon (aa 1) to residue 809 in HCV, and will be spliced into GBV-B in lieu of the segment encoding aa 1-732 in the GBV-B clone. The complementary chimeras to be constructed within the background of HCV will involve exchanges of the same segments of the genomes.

Example 17

Characterization of Structural Protein Chimeras

Prior to being evaluated for infectivity in tamarins, the processing of these chimeric polyproteins will be examined in coupled transcription/translation reactions supplemented with microsomal membranes, as described in the preceding sections for the proteinase and other proposed chimeras. If these results confirm that the polyprotein is processed as expected, with production of glycosylated E1 and E2 proteins from each of the chimeras (and seen in similar experiments with HCV proteins), studies would proceed in tamarins as previously described. The results of these studies may provide novel information on the basis of the host range differences that exist between HCV and GBV-B. If these results suggest that the envelope proteins play a critical role in determining host range, additional experiments could be carried out with these chimeras in chimpanzees (which are permissive for HCV but apparently not for GBV-B).

Example 18

Further Characterization of Rescued Chimeric Viruses

Where infection with chimeric viruses is induced in animals that are injected within the liver with synthetic RNA, this virus will be passaged in GBV-B naïve tamarins to further characterize the nature of the infection induced by the chimera. This will be accomplished by taking a pool of the 3 highest titer GBV-B RNA-containing serum specimens from the animal that was successfully transfected with RNA, and inoculating 1 mL of a 1:100 dilution of this pool intravenously into two susceptible animals. These animals will be monitored for infection and liver disease. These animals will be followed until resolution of the viremia and appearance of antibodies detectable in immunoblots with GST-NS3 protein expressed in E. coli, or for at least 6 months should an animal sustain a chronic infection. RT-PCR amplification of chimeric segments of the genome may be employed to determine whether the altered phenotype results from mutations within the heterologous portion of the genome.

Example 19

Use of GBV-B as Model for HCV

GBV-B and/or GBV-B/HCV chimeras can be used as a model for HCV. Such studies will allow one to investigate the mechanisms for the different biological properties of these viruses and to discover and investigate potential inhibitors of specific HCV activities (e.g., proteinase) required for HCV replication.

Example 20

Use of GBV-B/HCV Chimeras to Test Candidate HCV NS3 Proteinase Inhibitors or Other Inhibitors of HCV GBV-B/HCV viruses can be used in preclinical testing of candidate HCV NS3 proteinase inhibitors or other inhibitors of HCV.

1. Candidate Substances

As used herein the term "candidate substance" refers to any molecule that is capable of modulating HCV NS3 proteinase activity or any other activity related to HCV infection. The candidate substance may be a protein or fragment thereof, a small molecule inhibitor, or even a nucleic acid molecule. It may prove to be the case that the most useful pharmacological compounds for identification through application of the screening assay will be compounds that are structurally related to other known modulators of HCV NS3 proteinase activity. The active compounds may include fragments or parts of naturally-occurring compounds or may be only found as active combinations of known compounds that are otherwise inactive. However, prior to testing of such compounds in humans or animal models, it will be necessary to test a variety of candidates to determine which ones have potential.

Accordingly, the active compounds may include fragments or parts of naturally-occurring compounds or may be found as active combinations of known compounds that are otherwise inactive. As such, the present invention provides screening assays to identify agents that are capable of inhibiting proteinase activity in a cell infected with chimeric GBV-B/HCV viruses containing the HCV proteinase. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of proteinases or from structural studies of the HCV proteinase.

The candidate screening assays are simple to set up and perform. Thus, in assaying for a candidate substance, after obtaining a chimeric GBV-B/HCV virus with infectious properties, a candidate substance can be incubated with cells infected with the virus, under conditions that would allow measurable changes in infection by the virus to occur. In this fashion, one can measure the ability of the candidate substance to prevent or inhibit viral replication, in relationship to the replication ability of the virus in the absence of the candidate substance. In this fashion, the ability of the candidate inhibitory substance to reduce, abolish, or otherwise diminish viral infection may be determined.

"Effective amounts" in certain circumstances are those amounts effective to reproducibly reduce infection by the virus in comparison to the normal infection level. Compounds that achieve significant appropriate changes in activity will be used. Candidate compounds can be administered by any of a wide variety of routes, such as intravenously, intraperitoneally, intramuscularly, orally, or any other route typically employed.

It will, of course, be understood that all the screening methods of the present invention are useful in themselves notwithstanding the fact that effective candidates may not be found. The invention provides methods of screening for such candidates, not solely methods of finding them.

2. In Vitro Assays

In one particular embodiment, the invention encompasses in vitro screening of candidate substances. Using a cell line that can propagate GBV-B in culture, in vitro screening can be used such that GBV-B or HCV virus production or some indicator of viremia is monitored in the presence of candidate compounds. A comparison between the absence and presence of the candidate can identify compounds with possible preventative and therapeutic value.

3. In Vivo Assays

The present invention also encompasses the use of various animal models to test for the ability of candidate substances to inhibit infection by HCV. This form of testing may be done in tamarins.

The assays previously described could be extended to whole animal studies in which the chimeric virus could be used to infect a GBV-B permissive primate, such as a tamarin. One would then look for suppression of viral replication in the animal, and a possible impact on liver disease related to replication of the infectious chimeric virus. The advantage of this in vivo assay over present available assays utilizing HCV infection in chimpanzees is the reduced cost and greater availability of GBV-B permissive nonhuman primate species.

Treatment of animals with test compounds will involve the administration of the compound, in an appropriate form, to the animal. Administration will be by any route that could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, intraperitoneal injection, and oral administration.

Determining the effectiveness of a compound in vivo may involve a variety of different criteria. Such criteria include, but are not limited to, survival, reduction of rate of infection, arrest or slowing of infection, elimination of infection, increased activity level, improvement in liver function, and improved food intake.

Example 21

Use of Infectious GBV-B/HCV Chimeras as Vaccines

Infectious GBV-B/HCV chimeras expressing HCV envelope proteins will have utility as a vaccine immunogen for hepatitis C. Such clones clearly have the potential to be constructed as chimeras including relevant hepatitis C virus sequences in lieu of the homologous GBV-B sequence, providing unique tools for drug discovery efforts.

Chimeric viruses containing the envelope proteins of hepatitis C virus (as described in the attached) would confer the antigenic characteristics of hepatitis C virus on the chimera. These chimeras may have the ability to replicate in chimpanzees (and thus humans) by virtue of the fact that the chimeric envelope is now able to interact with the human hepatocyte cell surface, a necessary first step in virus replication. Therefore, the chimeric virus, while able to infect and replicate in humans, may not cause much or any disease-the reasoning here is that the genetic backbone of the chimera that encodes the nonstructural proteins of GBV-B has not evolved for replication in human cells and thus may not replicate well. Thus, the chimera may have limited replication ability, cause no disease, but still elicit immunity to the surface envelope proteins of HCV and thus have potential as a hepatitis C vaccine. These chimeras can be tested for their ability to promote immunity to HCV through an immune response.

Example 22

Construction of a GBV-B Infectious Clone

A genome-length cDNA copy of the complete GB virus B (GBV-B) genome sequence, including the novel 3' terminal sequence, was assembled from fragments amplified by reverse transcription-polymerase chain reaction (RT-PCR) from viral RNA present in a 0.2 µl aliquot of infectious serum (GB agent pool mystrax 666, 8/93) supplied by Dr. Jens Bukh of the National Institutes of Health. The serum sample was diluted with 100 µl of fetal calf serum and extracted using the Trizol system (GIBCO/BRL). The pellet was dissolved in 10 mM dithiothreotol containing 20 u/mL RNasin (Promega). The selection of primers for cDNA synthesis and PCR amplification was based on the published sequence of GBV-B (Simons et al., 1995). RT/PCR was carried out using Superscript Reverse Transcriptase (GIBCO/BRL) and the Advantage cDNA PCR Kit (Clontech). Four subgenomic regions were amplified covering the entire published GBV-B genome sequence. A fifth subgenomic region included the novel 3' terminal sequence that was identified in our laboratory. The oligonucleotide primer sets (listed 5'→3') used for amplification of the individual regions included:

Primer 1: CGGGATCCCGTAATACGACTCACTATA-GACCACAAACACTCCAGTTTG (SEQ ID NO:3)

Primer 2: GTGGAATTCACAGCGTCATA (SEQ ID NO:4)
   (Places a T7 RNA polymerase promoter sequence immediately upstream of the GBV-B sequence; the amplified segment extends from the 5' terminus of the viral genome to the unique EcoRI site at position 1978.)

Primer 3: TGTGAATTCCACTCTCCTACC (SEQ ID NO:5)

Primer 4: TTATCGATTGCAGCAACCATG (SEQ ID NO:6)

(Overlapping EcoRI site at position 1978 and the unique ClaI site at 5327.)

Primer 5: CATGGTTGCTGCAATCGATAAGCTGAA-GAGTACAATAAC (SEQ ID NO:7)

Primer 6: GACAACAGACGCTTGACACG (SEQ ID NO:8)

(Overlapping the Cla I site at 5327 and a unique Sal I site at 7847 in the published sequence: however, the Sal I site was not present in the amplified GBV-B sequence, and was thus introduced into the cDNA using the QuickChange Site-directed Mutagenesis Kit (Stratagene).)

Primer 7: CTGTCATGGGAGATGCGTAC (SEQ ID NO:9)

Primer 8: CGAGCTCGAGCACATCGCGGGGTCGT-TAAGCCCGGGGTCTCC (SEQ ID NO:10)

(Overlapping the Sal I site at 7847 and the published 3' end of the genome.)

Primer 9: GACAACAGACGCTTGACACG (SEQ ID NO:11)

Primer 10: CCGACTCGAGAATTCGGCCCTGCAGGC-CACAACAGTCTCGCGAGTTTTTAATT CCAAGCGGGGGTTGCCCTCCGCTTGGAA-CAAAAACCGGGGTGCAGCCCTTGG TAC (SEQ ID NO:12)

(Overlaps product of primers 7 and 8 and extends to the novel 3' terminal sequence; includes an Xho I site at the 3' terminus of the GBV-B sequence to aid subsequent manipulations.)

RT-PCR products were gel-purified using the QIAquick Gel Extraction Kit (Qiagen) and ligated into a plasmid vector with the PstBlue-1 Perfectly Blunt Cloning Kit (Novagene). Bacterial colonies were screened for plasmid DNAs with the correct insert size. Those harboring an insert of the approximate correct size were subjected to diagnostic restriction analysis. cDNA inserts generating the appropriate restriction patterns were sequenced in both directions using an ABI DNA sequencer, and those with sequences closest to the published GBV-B sequence (Simons et al., 1995) were selected for subsequent assembly into the full-length clone.

The cloned overlapping cDNA fragments were assembled into the pACNR1180 plasmid using the unique restriction sites noted in the primer descriptions. The final, fully assembled plasmid bearing a 9.4 kb cDNA GBV-B insertion was subjected to DNA sequencing to confirm the validity of the construction and the absence of any mutations or errors in the sequence that may have been introduced during the assembly process. The sequence of the GBV-B infectious cDNA is shown in SEQ ID NO:2.

Plasmid DNA containing the GBV-B cDNA was purified by isopycnic centrifugation on a CsCl gradient and isolated by ethanol precipitation. The plasmid DNA was linearized at the 3' terminus of the cDNA insert by digestion with Xho I. Two μg of the linearized DNA was used as template in an in vitro transcription reaction using the Ambion T7 MEGAscript Kit according to the manufacturer's instructions. The integrity of the resultant synthetic RNA product was confirmed by nondenaturing agarose gel electrophoresis.

Approximately 60 μg of RNA transcribed from the GBV-B cDNA clone was diluted in phosphate buffered saline and injected under direct visualization at laparotomy into the liver of a healthy tamarin without a prior history of GBV-B infection (*Saguinus oedipus*). Serum samples were collected from the animal weekly beginning at 2 weeks post-inoculation and tested for the presence of GBV-B RNA by real-time quantitative RT-PCR (TaqMan assay). Results are shown in the following table.

| Week Postinoculation | Genome equivalents/ml |
|---|---|
| 0 | 0 |
| 2 | $8.3 \times 10^3$ |
| 3 | $6.6 \times 10^5$ |
| 4 | $4.6 \times 10^8$ |

The presence of high and increasing titers of viral RNA in the serum of this animal between 2-4 weeks postinoculation confirms the infectivity of the full-length cDNA clone containing the novel 3' terminal sequence. The presence of viremia demonstrated that viral replication had ensued following the delivery of the synthetic viral RNA to hepatocytes.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents, which are both chemically and physiologically related, may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,800,159
U.S. Pat. No. 4,883,750
U.S. Pat. No. 5,279,721
U.S. Pat. No. 5,807,670
EPA No. 320,308
EPA No. 329,822
GB Application No. 2,202,328
PCT/US87/00880
PCT/US89/01025
WO 88/10315
WO 89/06700
WO 90/07641
Al, R H., Xie, Y., Wang, Y., and Hagedon: Expression of recombinant hepatitis C NS5B in *E coli. Virus Res* 53 141-149, 1998.
Alter, M. J. Epidemiology of hepatitis C. Hepatology 26 625-655, 1997.
Beard, M R., Abell, G., Sangar, D V., Honda, M., Garland, M., Carroll, A R., and Lemon S M: An Infectious Molecular Clone of a Japanese Genotype 1b Hepatitis C Virus. *Hepatology, In press,* 1999.

Behrens, S E., Tomei, L., and De Francesco: Identification and properties of the RNA dependent RNA polymerase of hepatitis C virus. *EMBO J* 15 12-22, 1996.

Chambers, T J, Nestrorowicz, A., Mason, P W., and Rice, C M. Yellow fever/Japanese encephalitis chimeric viruses. Construction and biological properties. *J Virol* 73 3095-3101, 1999.

Choo, Q.-L., G. Kuo, G. Ralston, R., Weiner, A., Chien, D., VanNest, G., Han, P., Berger, K. Thudium, K., Kuo, C., Kansopon, J., McFarland, J., Tabrizi, A., Ching, K., Moss, B. Cummins, L. B., Houghton, M. and Muchmore, E., Vaccination of chimpanzees against infection by the hepatitis C virus. *Proc Natl Acad Sci USA* 91:1294-1298, 1994.

Consensus Development Panel. National Institutes of Health Consensus Development Conference Panel statement: Management of hepatitis C. *Hepatology* 26, Supplement 1[3], 2S-10S, 1997.

Farci, P., Alter, H. J., Govindarajan, S., Wong, D. C., Engle, R., Lesniewski, R. R., Mushahwar, I. K., Desai, S. M., Miller, R. H., Ogata, N., and Purcell, R. H., Lack of protective immunity against reinfection with hepatitis c virus. *Science* 258 135-140. 1992.

Farci, P., London, W. T., Wong, D. C., Dawson, G. J., Vallari, D. S., Engle, R., and Purcell, R. H., The natural history of infection with hepatitis C virus (HCV) in chimpanzees: Comparison of serologic responses measured with first- and second-generation assays and relationship to HCV viremia. *The Journal of Infectious Diseases* 165, 1006-1011, 1992.

Filocamo, G., Pacinsh, L., and Migliacciog: Chimeric sindbis virus dependent on the NS3 protease of hepatitis C virus. *J Virol* 71 1417-27, 1997.

Frohman, *PCR PROTOCOLS: A GUIDE TO METHODS AND APPLICATIONS*, Academic Press, New York, 1990.

Frolov, I., McBride, M. S., and Rice, C. M., cis-acting RNA elements required for replication of bovine viral diarrhea virus-hepatitis C virus 5' nontranslated region chimeras. *RNA* 4, 1418-1435, 1998.

Grakoui et al., Characterization of the hepatitis C virus-encoded serine proteinase: determination of proteinase-dependent polyprotein cleavage sites. *J. Virol.* 67(5): 2832-43, 1993.

Grakoui et al., Expression and identification of hepatitis C virus polyprotein cleavage products. *J. Virol* 67(3):1385-95. 1993.

Hijikata, M., Mizushima, H., Akagi, T., Mori, S., Kakiuchi, N., Kato, N., Tanaka, T., Kimura, K., and Shimotohno, K: Two distinct protease activities required for the processing of a putative non-structural precursor protein of hepatitis C virus. *J Virol* 67 4665-4675, 1993.

Honda, M., Brown, E A., and Lemon, S M: Stability of a stem-loop involving the initiator AUG controls the efficiency of internal initiation of translation on hepatitis C virus RNA. *RNA* 2 955-956, 1996.

Karayiannis, P., Petrovic, L M., Fry, M., Moore, D., Enticott, M., McGarvey, M J., Scheuer, P J., and Thomas, H C: Studies of GB hepatitis agent in tamarins. *Hepatology* 9 186-192, 1989.

Kim, J. L., Morgenstern, K. A., Lin, C., Fox, T., Dwyer, M. D., Landro, J. A., Chambers, S. P., Markland, W., Lepre, C. A., O'Malley, E. T., Harbeson, S. L., Rice, C. M., Murcko, M. A., Caron, P. R., and Thomson, J. A.: Crystal structure of the hepatitis C virus NS3 protease domain complexed with a synthetic NS4A cofactor peptide. *Cell* 87, 343-355, 1996.

Kolykhalov, A A,. Agapov, E N., Blight, K., Mihalik, S M., Feinstone, S M., and Rice, C M: Transmission of hepatitis C by intrahepatic inoculation of transcribed RNA. *Science* 277 570-574, 1997.

Kolykhalov, A A., Feinstone, S M., and Rice, C M: Identification of a highly conserved element at the 3' terminus of hepatitis C virus genome RNA. *J Virol* 70 3363-3371, 1996.

Landt, O., Grunert, H. P., Hahn, U. A general method for rapid site-directed mutagenesis using the polymerase chain reaction. *Gene* 96: 125-128, 1990.

Lemon, S. M. and Honda, M. (1997) Internal ribosome entry sites within the RNA genomes of hepatitis C virus and other flaviviruses. *Seminars in Virology* 8, 274-288, 1997.

Lindenbach, B. D. and Rice, C. M. Genetic interaction of flavivirus nonstructural proteins NS1 and NS4A as a determinant of replicase function [In Process Citation]. *J Virol* 73, 4611-4621, 1999.

Lu, H.-H. and Wimmer, E. Poliovirus chimeras replicating under the translational control of genetic elements of hepatitis C virus reveal unusual properties of the internal ribosomal entry site of hepatitis C virus. *Proc Natl Acad Sci USA* 93, 1412-1417, 1996.

Muerhoff, A S., Leary, T P., Simons, J N., Pilot-Matias, T J., Dawson, G J., Erker, J C., Chalmers, M L., Schlauder, G G., Desai, S M., and Mushahwar, I K: Genomic organisation of GB viruses A and B: Two new members of the flaviviridae associated with GB agent hepatitis. *J Virol* 69 5621-5630, 1995.

Neumann, A. U., Lam, N. P., Dahari, H., Gretch, D. R., Wiley, T. E., Layden, T. J., and Perelson, A. S. Hepatitis C viral dynamics in vivo and the antiviral efficacy of interferon-alpha therapy. *Science* 282, 103-107, 1998.

Pletnev, A. G., Bray, M., Huggins, J. and Lai, C. J. Construction and characterization of chimeric tick-borne encephalitis and dengue viruses. *Proc. Natl. Acad Sci USA* 89; 10532-10536, 1992.

Remington's Pharmaceutical Sciences, 15$^{th}$ Edition, pages 1035-1038 and 1570-1580.

Reynolds, J. E., Kaminiski, A., Kettinen, H. J., Carroll, A. R., Rowlands, D. J., and Jackson, R. J. Unique features of internal initiation of hepatitis C virus RNA translation. *EMBO J.* 14, 6010-6020, 1995.

Rijnbrand, R., Abell G, and Lemon, S. M. Mutational analysis of the GB virus B internal ribosome entry site. Submitted for publication, 1999.

Sambrook, et al., *Molecular Cloning, A Laboratory Manual*, 2nd ed., Cold Spring Harbor Laboratory, Cold Spring, Harbor, N.Y., 1989.

Scarselli, E., Urbani, A., Sbardellati, A., Tomei, L., De Francesco, R., and Traboni: GB virus B and hepatitis C virus share substrate specificity. *J Virol* 71 4985-4989, 1997.

Schlauder, G G., Dawson, G J., Simons, J M., Pilot-Matias, T J., Gatierrez, R A., Heynen, C A., Knigge, M F., Kurpiewski, G S., Buijk, S L., Leary, T P., Muerhoff, A S., Desai, S M., and Mushahuar, I K; Molecular and serological analysis in the transmission of the GB hepatitis agent. *J Med Virol* 46 81-90, 1995.

Shaffer, D. R., Emerson, S. U., Murphy, P. C., Govindarajan, S., and Lemon, S. M. A hepatitis A virus deletion mutant which lacks the first pyrimidine-rich tract of the 5' non-translated RNA remains virulent in primates after direct intrahepatic nucleic acid transfection. *J Virol* 69, 6600-6604, 1995.

Simons, J N., Pilot-Matias, T J., Leary, S L., Dawson, G J., Desai, S M., Schlauder, G G., Muerhoff, A S., Erker, J C., Buijk, S L., Chalmers, M L., Van Saint, C L., and Mushahwar, I K: Identification of two flavivirus like genomes in the GB hepatitis agent. *Proc Natl Acad Sci* 92 3401-3405, 1995.

Tanaka, T., Kato, N., Cho, M J., and Shimothono, K: A novel sequence found at the 3' terminus of hepatitis C virus genome. *Biochem Biophys Res Comm* 215 744-749, 1995.

Teller, R., Bukh, J., Emerson, SU., Miller, R H., and Purcell, R H., Long PCR and it's application to hepatitis A, hepatitis B and hepatitis C virus genomes. *J Clin Micro* 34 3085-3091, 1996.

Todd, S., Towner, J S., Brown, DM., and Semler, B L: Replication competent picornaviruses with complete genomic RNA 3' non-coding deletions. *J Virol* 71 8868-74, 1997.

Yanagi, M., Purcell, R H., Emmerson, S U., and Bukh, J., Transcripts from a single full length clone are infectious when directly transfected into a liver of a chimpanzee. *Proc Natl Acad Sci USA* 16 8738-8743, 1998.

Yao, N. H., Hesson, T., Cable, M., Hong, Z., Kwong, A. D., Le, H. V., and Weber, P. C., Structure of the hepatitis C virus RNA helicase domain. *Nature Structural Biology* 4, 463-467, 1997.

Zhao, W D., Wimmer, E., and Lahser, F C. Poliovirus/hepatitis C virus (internal ribosome entry site-core) chimeric viruses: improved growth properties through modification of a proteolytic cleavage site and requirement for core RNA sequence but not for core related polypeptides. *J Virol* 73 1546-1554, 1999.

What is claimed is:

1. A method of producing a recombinant or chimeric GBV-B virus comprising:

introducing into a host cell a recombinant GBV-B or chimeric GBV-B viral genome comprising a 3' terminal sequence of GBV-B, wherein the 3' terminal sequence comprises 50 contiguous nucleotides from SEQ ID NO:1; and culturing said host cell under conditions where the 3' terminal sequence permits production of the virus from said genome.

2. The method of claim 1, wherein said 3' terminal sequence comprises 100 contiguous nucleotides from SEQ ID NO:1.

3. The method of claim 2, wherein said 3' terminal sequence comprises SEQ ID NO:1.

4. The method of claim 1, wherein said host cell is in an animal.

5. The method of claim 1, wherein said genome comprises recombinant RNA.

6. The method of claim 1, wherein said genome is encoded by recombinant DNA.

7. The method of claim 1, further comprising the step of isolating virus from said host cell.

8. The method of claim 7, wherein said virus is purified to homogeneity.

9. A method of producing a GBV-B or chimeric GBV-B virus comprising:

obtaining a virus produced by the method of claim 1;
introducing the virus into a second host cell; and
culturing said host cell under conditions permitting production of virus.

10. A method of producing a virus comprising:

introducing into a host cell a recombinant GBV-B or chimeric GBV-B viral genome comprising a 3' terminal sequence of GBV-B, wherein the 3' terminal sequence has at least 70% sequence identity to SEQ ID NO:1; and maintaining said host cell under conditions permitting production of a virus from said genome.

11. The method of claim 10, wherein the host cell is a liver cell.

12. The method of claim 11, wherein the liver cell is in an animal.

13. The method of claim 12, wherein the animal is a primate.

14. The method of claim 13, wherein the primate is a non-human primate.

15. The method of claim 13, wherein the primate is a tamarin.

16. The method of claim 11, wherein the 3' terminal sequence has at least 80% sequence identity to SEQ ID NO:1.

17. The method of claim 16, wherein the 3' terminal sequence has at least 90% sequence identity to SEQ ID NO:1.

18. The method of claim 17, wherein the 3' terminal sequence has at least 95% sequence identity to SEQ ID NO:1.

19. The method of claim 18, wherein the 3' terminal sequence is SEQ ID NO:1.

20. A method of producing a recombinant or chimeric GBV-B virus comprising:

introducing into a liver cell a recombinant GBV-B or chimeric GBV-B viral genome comprising a 3' terminal sequence of GBV-B, wherein the 3' terminal sequence has at least 70% sequence identity to SEQ ID NO:1; and maintaining said liver cell under conditions where the 3' terminal sequence permits production of the virus from said genome.

21. A method of replicating a recombinant chimeric GBV-B virus comprising:

introducing into a liver cell a recombinant GBV-B or chimeric GBV-B viral genome comprising a 3' terminal sequence of GBV-B, wherein the 3' terminal sequence has at least 70% sequence identity to SEQ ID NO:1; and maintaining said liver cell under conditions where the 3' terminal sequence permits replication of the recombinant viral genome.

22. The method of claim 21, wherein the 3' terminal sequence has at least 80% sequence identity to SEQ ID NO:1.

23. The method of claim 22, wherein the 3' terminal sequence has at least 90% sequence identity to SEQ ID NO:1.

24. The method of claim 23, wherein the 3' terminal sequence has at least 95% sequence identity to SEQ ID NO:1.

25. The method of claim 24, wherein the 3' terminal sequence is SEQ ID NO:1.

* * * * *